(12) United States Patent
Levit

(10) Patent No.: US 11,284,900 B2
(45) Date of Patent: Mar. 29, 2022

(54) GAS INFLATION DEVICES, SYSTEMS, AND METHODS

(71) Applicant: RENALPRO MEDICAL, INC., Palo Alto, CA (US)

(72) Inventor: Eran Levit, Amherst, NH (US)

(73) Assignee: RenalPro Medical, Anc., Santa Clara, CA (US)

( * ) Notice: Subject to any disclaimer, the term of this patent is extended or adjusted under 35 U.S.C. 154(b) by 36 days.

(21) Appl. No.: 16/447,827

(22) Filed: Jun. 20, 2019

(65) Prior Publication Data
US 2020/0100798 A1  Apr. 2, 2020

Related U.S. Application Data

(60) Provisional application No. 62/688,323, filed on Jun. 21, 2018.

(51) Int. Cl.
*A61B 17/12* (2006.01)
*A61M 25/10* (2013.01)

(52) U.S. Cl.
CPC .. *A61B 17/12136* (2013.01); *A61B 17/12109* (2013.01); *A61M 25/10182* (2013.11); *A61M 25/10186* (2013.11); *A61M 2025/1052* (2013.01)

(58) Field of Classification Search
CPC ....... A61B 17/12136; A61B 17/12109; A61M 25/10182; A61M 25/10186; A61M 2025/1052; A61M 25/10187; A61M 25/10184; A61M 39/10; A61M 5/155; A61M 5/145
See application file for complete search history.

(56) References Cited

U.S. PATENT DOCUMENTS

| 3,409,016 A | * | 11/1968 | Foley | A61M 25/10182 |
| | | | | 604/98.01 |
| 4,370,982 A | | 2/1983 | Reilly | |
| 4,655,749 A | * | 4/1987 | Fischione | A61M 25/10184 |
| | | | | 600/561 |
| 4,795,431 A | | 1/1989 | Walling | |

(Continued)

FOREIGN PATENT DOCUMENTS

WO  WO2019/246443 A1  12/2019

*Primary Examiner* — Julian W Woo
(74) *Attorney, Agent, or Firm* — Shay Glenn LLP

(57) ABSTRACT

Devices, systems, and methods for inflation are provided. Inflation devices include a housing, a compressed gas canister disposed therein, a syringe disposed within the housing, a plunger slidably disposed in the syringe having an unloaded position and a loaded position relative to the syringe, a puncture mechanism disposed within the housing and configured to open a fluid path between the compressed gas canister and the syringe, and a positive pressure mechanism disposed within the housing and operably coupled to the syringe. Engagement of the puncture mechanism puts the syringe into fluid communication with the compressed gas canister such that gas contained therein loads into the syringe and the plunger moves from the unloaded position and the loaded position. The positive pressure mechanism is configured to maintain the gas within the syringe at a positive pressure relative to ambient pressure in order to prevent air from entering the syringe after loading.

21 Claims, 27 Drawing Sheets

(56) References Cited

U.S. PATENT DOCUMENTS

| | | | |
|---|---|---|---|
| 4,976,725 A * | 12/1990 | Chin | A61M 3/00 |
| | | | 604/100.01 |
| 5,147,300 A * | 9/1992 | Robinson | A61M 25/104 |
| | | | 604/100.03 |
| 5,496,311 A * | 3/1996 | Abele | A61B 17/22 |
| | | | 606/28 |
| 6,575,937 B2 | 6/2003 | Hansen | |
| 6,942,678 B2 | 9/2005 | Bonnette et al. | |
| 7,195,610 B1 | 3/2007 | Flachbart | |
| 7,615,031 B2 | 11/2009 | Bonnette et al. | |
| 9,764,088 B2 | 9/2017 | Huculak et al. | |
| 10,300,252 B2 | 5/2019 | Lee et al. | |
| 10,441,291 B2 | 10/2019 | Koo et al. | |
| 2003/0078538 A1 | 4/2003 | Neale et al. | |
| 2016/0193455 A1 | 7/2016 | Timothy | |
| 2017/0136174 A1 | 5/2017 | Levy et al. | |

\* cited by examiner

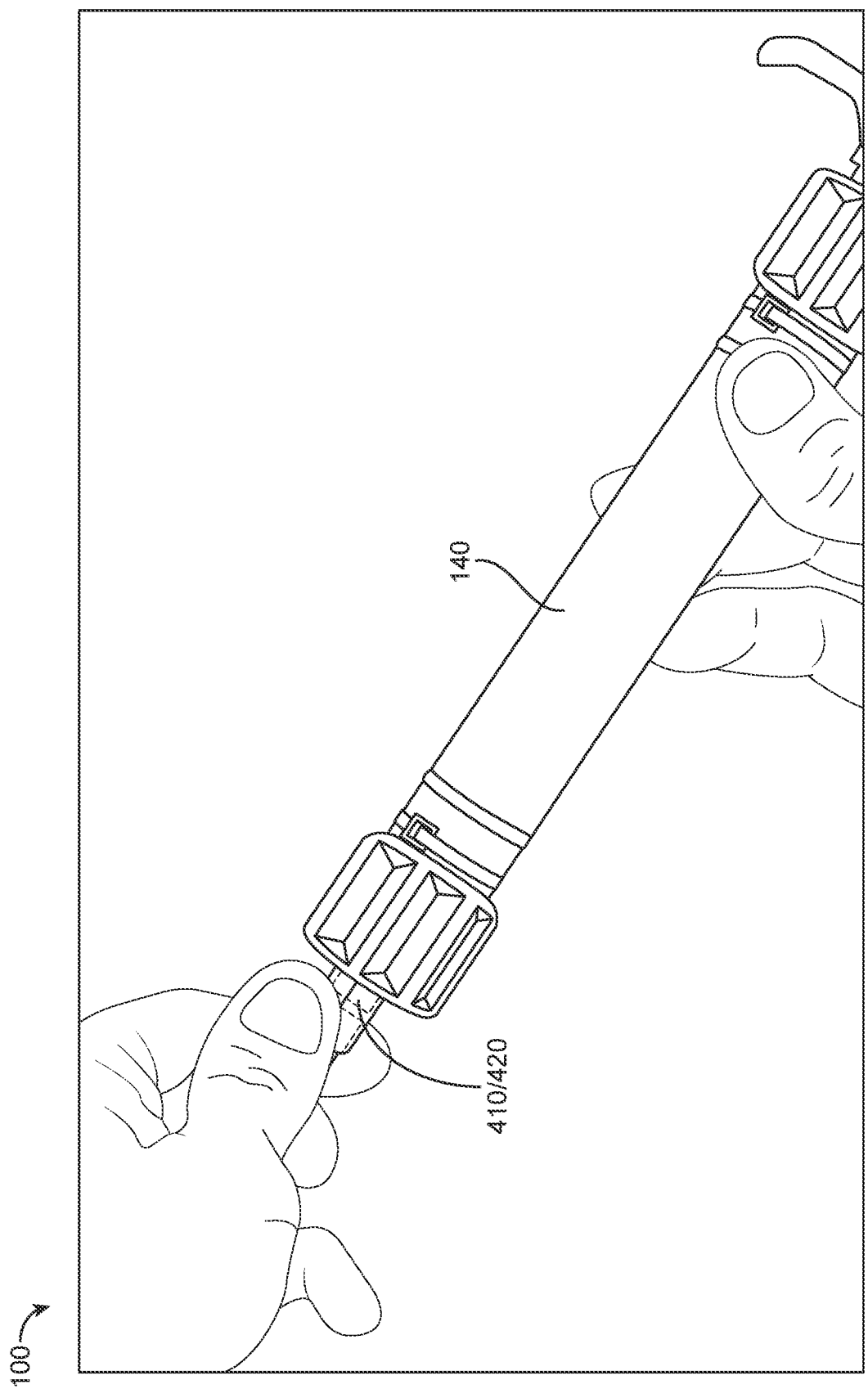

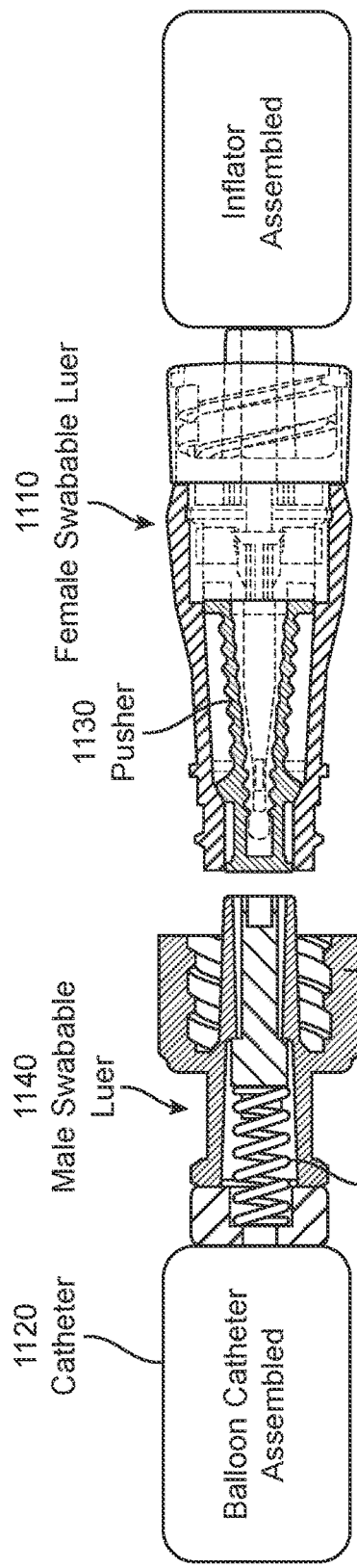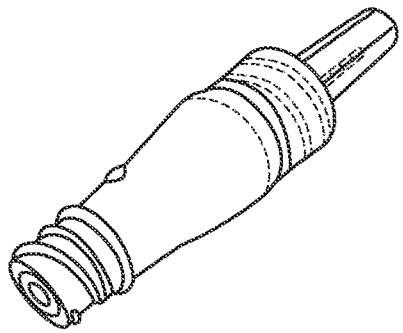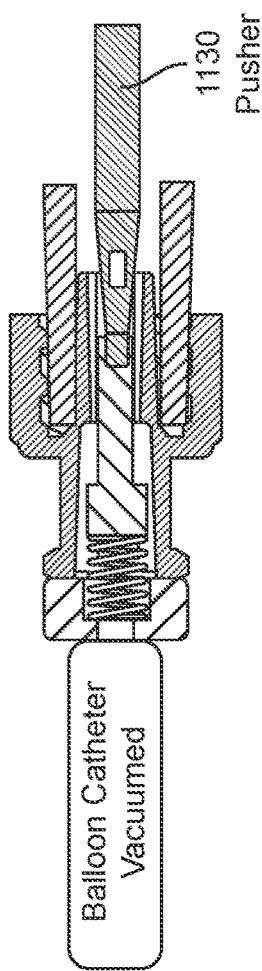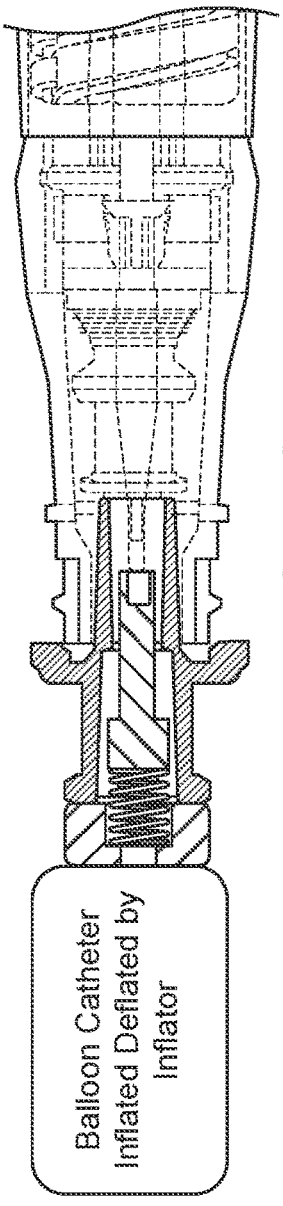

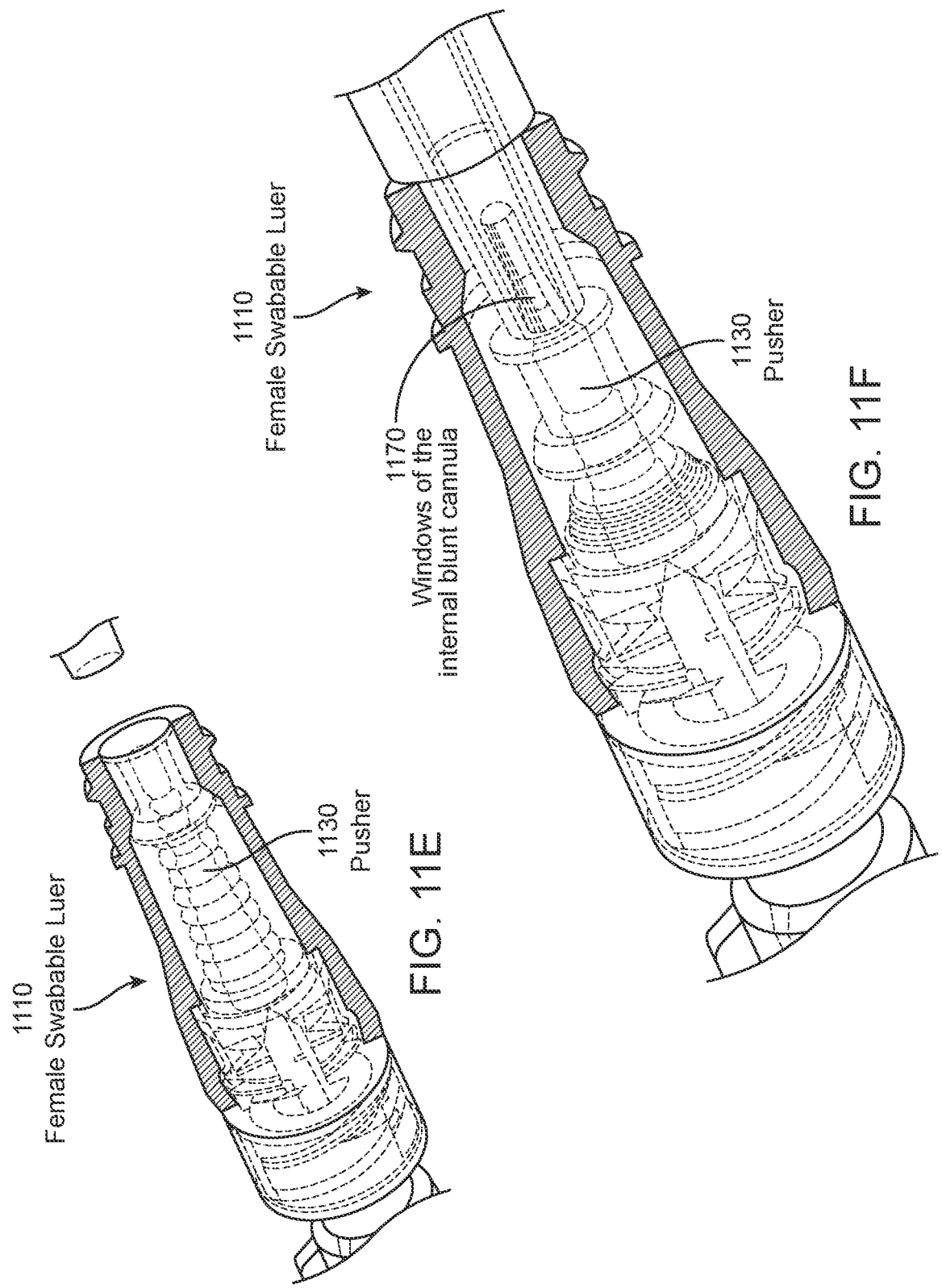

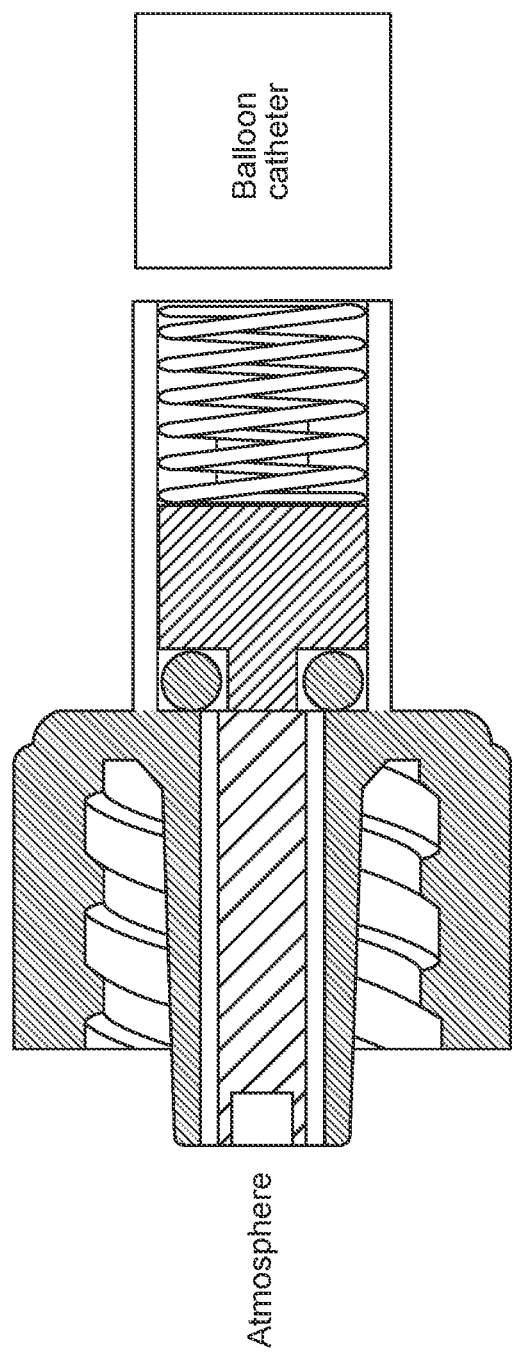

GAS INFLATION DEVICES, SYSTEMS, AND METHODS

CROSS-REFERENCE

This application claims the benefit of U.S. Provisional Application No. 62/688,323, filed Jun. 21, 2018, the entire contents of which are incorporated herein by reference.

The subject matter of the present application is related to the subject matter of U.S. patent application Ser. No. 15/140,502 (filed Apr. 28, 2016), Ser. No. 15/189,460 (filed Jun. 22, 2016), Ser. No. 15/969,050 (filed May 2, 2018), PCT Application Nos. PCT/US2014/072302 (filed Dec. 23, 2014) and PCT/US2017/031153 (filed May 4, 2017), and U.S. Provisional Application No. 62/688,233 (filed Jun. 21, 2018), the full contents of which are incorporated herein by reference.

BACKGROUND

Many medical procedures involve the use of inflation devices to provide gas to balloon catheters. Gas inflation may be useful in inflation of balloon catheters when radiation is involved as gas may have a lower attenuation of radiation than a liquid. Gas inflation may also be useful in situations where rapid inflation or deflation of the balloon catheter is desired, as the density of gas may be lower than a liquid resulting in a faster flow rate. While gas inflation may be desired in at least some instances, current devices for providing gas to a balloon catheter are typically much more complicated than those for liquid inflation when the gas is not air. For example, built-in carbon dioxide plumbing systems common in many medical facilities may be connected to a reduction valve to fill an inflation device. However, such systems may be physically cumbersome and may require significant time and effort to prepare. In another example, a syringe may be manually filled with gas transferred from a pressurized gas canister connected directly to the syringe tip. In at least some instances, however, multiple connections may be used to couple the syringe to the canister, and/or manual retraction of the syringe plunger may be which may present multiple opportunities for failure and gas escaping from the syringe and/or air leaking into the syringe. Additionally, such inflation devices typically require disconnection of the syringe from the gas canister, and subsequent connection to a balloon catheter in order to inflate the balloon catheter, which may also allow for gas to escape from and/or air to leak into the syringe prior to and/or while being attached to the balloon catheter.

References relevant to the present disclosure may include: U.S. Pat. Nos. 7,195,610, 9,764,088, US20030078538, U.S. Pat. Nos. 4,795,431, 6,575,937, 4,370,982, US20160193455, US20170136174, U.S. Pat. Nos. 6,942,678, and 7,615,031.

SUMMARY

It would therefore be desirable to provide an inflation device which may be used to fill a syringe with a gas without allowing gas to escape and/or air to enter the device before, during, or after filling the device, and/or before, during, or after inflating the balloon. At least some of these objectives may be met by the embodiments described herein.

Aspects of the present disclosure provide inflation devices. An exemplary inflation device may comprise a housing, a compressed gas canister disposed within the housing and containing a gas, and a syringe disposed at least partially within the housing and comprising a plunger slidably disposed therein, and a puncture mechanism disposed within the housing. The puncture mechanism may be configured to open a fluid path between the compressed gas canister and the syringe. Optionally, a positive pressure mechanism may be disposed within the housing and operably coupled to the syringe. The plunger may have an unloaded position and a loaded position relative to the syringe. The syringe may have a first position and a second position relative to the puncture mechanism within the housing. Actuation of the syringe from the first position to the second position may engage the puncture mechanism to put the syringe into fluid communication with the compressed gas canister such that the gas contained therein may be loaded into the syringe and the plunger may be moved from the unloaded position and the loaded position. The positive pressure mechanism may be configured to maintain the gas within the syringe at a positive pressure relative to ambient pressure in order to prevent air from entering the syringe after loading.

The puncture mechanism may comprise a pin, a needle, and/or a hollow tube.

The positive pressure mechanism may comprise a one-way valve, a duck valve, and/or a plastic rubber diaphragm.

The gas may comprise carbon dioxide. In some embodiments, the gas may be pure carbon dioxide.

The compressed gas cartridge may be configured to be removed from the housing and replaced.

The device may further comprise a handle coupled to the housing. The handle may have a first handle position and a second handle position. Actuation of the handle from the first handle position to the second handle position may actuate the syringe from the first position to the second position.

The device may further comprise an outlet port in a distal tip of the housing. The outlet port may be fluidly coupled to the syringe. The distal tip may be configured to be coupled to a catheter such that depression of the plunger from the loaded position towards the unloaded position may cause the gas loaded in the syringe to be injected into the catheter via the outlet port. The device may further comprise a time-delayed release mechanism operably coupled to the plunger. The time-delayed release mechanism may be configured to actuate the plunger from a depressed position to the loaded position after a pre-determined amount of time following depression of the plunger. The depressed position may be the unloaded position. The distal tip may comprise a catheter fitting. The catheter fitting may comprise a custom female connector configured to prevent coupling of the distal tip to an intravenous line. The device may be configured for selectively inflating and deflating a balloon of a balloon catheter. The device may further comprise a one-way fitting coupled to the distal tip. The one-way fitting may be configured to prevent the distal tip from being coupled to a catheter. The one-way fitting may be configured to be removed to expose the distal tip only when the syringe is in the second position. The device may further comprise a protection cap disposed around the one-way fitting and coupled to the housing. The protection cap may be configured to prevent removal of the one-way fitting when the syringe is in the first position and allow removal of the one-way fitting when the syringe is in the second position. The protection cap may be fixedly coupled to the housing when the syringe is in the first position. Actuation of the syringe from the first position to the second position may align a release mechanism of the protection cap and allows the protection cap to be removed from the housing.

The device may further comprise a stopper adjacent the plunger. The stopper may be configured to prevent the plunger from moving past the loaded position when the gas is loaded into the syringe. The stopper may be adjustable so as to set the loaded position of the plunger to a predetermined volume.

The device may further comprise a pressure relief mechanism fluidly coupled to the syringe. The compressed gas cartridge may be configured to hold a first volume of gas that is greater than a second volume of gas which is loaded into the syringe. The pressure relief mechanism may be configured to release excess gas after the puncture mechanism is engaged and the syringe is loaded with the second volume of gas. The pressure relief mechanism may comprise a duck valve.

The first position of the syringe may comprise a first rotational position of the syringe relative to the puncture mechanism. The second position of the syringe may comprise a second rotational position of the syringe relative to the puncture mechanism different from the first rotational position.

Aspects of the present disclosure also provide methods for inflating a balloon catheter. In an exemplary method, an inflation device may be provided. The inflation device may comprise a housing, a compressed gas cartridge containing a gas disposed within the housing, a syringe disposed within the housing, and a puncture mechanism disposed within the housing. The syringe may have a first position and a second position relative to the puncture mechanism within the housing. Actuation of the syringe from the first position to the second position may engage the puncture mechanism to put the syringe into fluid communication with the compressed gas canister such that the gas contained may be loaded into the syringe. The compressed gas cartridge may be punctured with the puncture mechanism in response to an actuation of the syringe from the first position to the second position, thereby loading the syringe with the gas. Air may be prevented from entering the syringe by maintaining the gas at a positive pressure relative to ambient pressure relative to ambient pressure after loading the syringe with the gas.

The puncture mechanism may comprise a pin, a needle, or a hollow tube.

The gas may comprise carbon dioxide. In some embodiments, the gas may be pure carbon dioxide.

Actuating the syringe from the first position to the second position may comprise actuating a handle coupled to the housing from a first handle position to a second handle position.

A distal tip of the inflation device may be coupled to a catheter. The distal tip may comprise an outlet port in fluid communication with the syringe. An expandable member of the catheter may be positioned adjacent renal artery ostia of a patient. The gas may be injected from the syringe into the catheter via the outlet port and inflating an expandable member of the catheter. Injecting the gas may comprise depressing a plunger disposed within the syringe from a loaded position towards an unloaded position. After injecting the gas, the compressed gas cartridge may be removed from the housing. The balloon may be deflated. Deflating the balloon may comprise actuating a plunger disposed within the syringe from a depressed position to a loaded position. The balloon may be deflated a pre-determined amount of time after injecting the gas and inflating the balloon. The distal tip may be prevented from being coupled to the catheter prior to actuation of the syringe from the first position to the second position. The inflation device may comprise a one-way fitting coupled to the distal tip. The one-way fitting may be configured to be removed to expose the distal tip only when the syringe is in the second position. The one-way fitting may be removed after actuating the syringe. The inflation device may comprise a protection cap disposed around the one-way fitting and coupled to the housing. The protection cap may be configured to prevent removal of the one-way fitting when the syringe is in the first position and allow removal of the one-way fitting when the syringe is in the second position. The protection cap may be removed after actuating the syringe.

A loading volume of the syringe may be adjusted to a pre-determined volume before actuating the syringe.

A volume of gas loaded into the syringe may be adjusted to a pre-determined volume after actuating the syringe.

The compressed gas cartridge may be configured to hold a first volume of gas that is greater than a second volume of gas which is loaded into the syringe. Excess gas may be released after the puncture mechanism is engaged and the syringe is loaded with the second volume of gas.

Actuating the syringe from the first position to the second position may comprise rotating the syringe from the first position to the second position.

Aspects of the present disclosure may also provide inflation devices. An exemplary inflation device may comprise a housing, a compressed gas canister disposed within the housing and containing a gas, and a syringe disposed at least partially within the housing and comprising a plunger slidably disposed therein, and a puncture mechanism disposed within the housing. The puncture mechanism may be configured to open a fluid path between the compressed gas canister and the syringe. Optionally, a distal tip of the housing may comprise an outlet port therein. The outlet port may be fluidly coupled to the syringe. The plunger may have an unloaded position and a loaded position relative to the syringe. The syringe may have a first position and a second position relative to the puncture mechanism within the housing. Actuation of the syringe from the first position to the second position may engage the puncture mechanism to put the syringe into fluid communication with the compressed gas canister such that the gas contained therein may be loaded into the syringe and the plunger may be moved from the unloaded position and the loaded position. The distal tip may be configured to be coupled to a catheter. Depression of the plunger from the loaded position towards the unloaded position may cause gas loaded in the syringe to be injected into the catheter via the outlet port.

Aspects of the present disclosure also provide methods for inflating a balloon catheter. In an exemplary method, an inflation device may be provided. The inflation device may comprise a housing, a compressed gas cartridge containing a gas disposed within the housing, a syringe disposed within the housing, and a puncture mechanism disposed within the housing. The syringe may have a first position and a second position relative to the puncture mechanism within the housing. Actuation of the syringe from the first position to the second position may engage the puncture mechanism to put the syringe into fluid communication with the compressed gas canister such that the gas contained may be loaded into the syringe. The compressed gas cartridge may be punctured with the puncture mechanism in response to an actuation of the syringe from the first position to the second position, thereby loading the syringe with the gas. A distal tip of the inflation device may be coupled to a catheter. The distal tip may comprise an outlet port in fluid communication with the syringe. A gas may be injected from the syringe into the catheter via the outlet port and inflating a balloon fluidly coupled to the catheter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIGS. 10A-10L show various steps involved in loading and using the inflation device of FIG. 9 to inflate a balloon of a balloon catheter, according to many embodiments.

FIGS. 11A-11G show exemplary connection fittings for the distal tip of the inflation device and a catheter, according to many embodiments.

DETAILED DESCRIPTION

Figure 1:
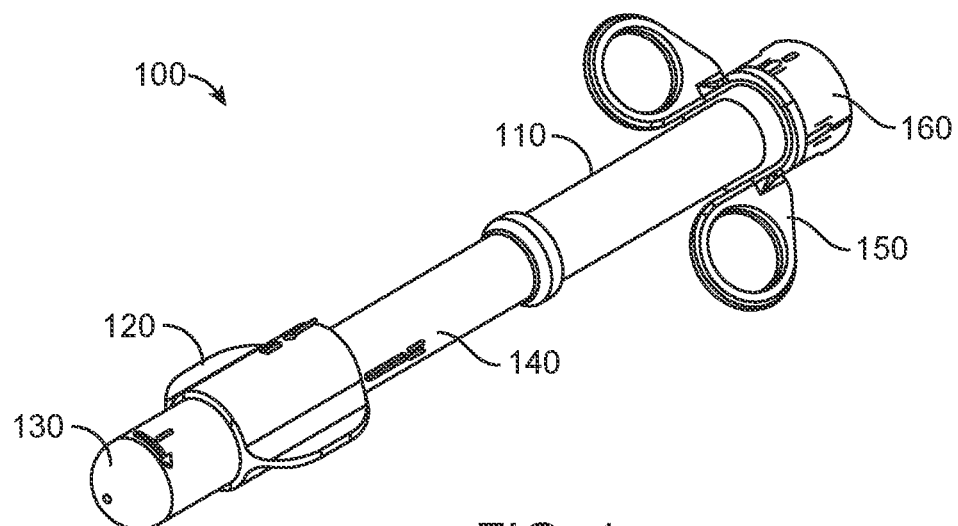
FIG. 1 shows a perspective view of an inflation device, according to many embodiments.

While various embodiments of the present disclosure have been shown and described herein, it will be obvious to those skilled in the art that such embodiments are provided by way of example only. Numerous variations, changes, and substitutions may occur to those skilled in the art without departing from the scope of the present disclosure. It should be understood that various alternatives to the embodiments of the present disclosure may be employed.

Provided herein are devices, systems, and methods loading a syringe of an inflation device with a compressed gas and/or using said syringe (and/or inflation device) to inject said gas into another device coupled thereto.

The inflation devices, systems, and methods described herein may be configured for selectively inflating and deflating a medical balloon, such as a balloon of a balloon catheter. The inflations, systems, and methods described herein may be used to selectively inflation and deflate a wide variety of balloon catheters such as dilation balloon catheters, centering balloon catheters, anchoring balloon catheters, angioplasty balloon catheters, stent placement balloon catheters, aorta occlusion balloon catheters, renal occlusion balloon catheters, pressure monitoring balloon catheters, biofeedback balloon catheters, atrial defect sizing balloon catheters, and the like.

While the inflation devices, systems, and methods described herein are discussed with relation to inflating a balloon catheter, it will be understood by one of ordinary skill in the art that the devices, systems, and methods described herein may be used in to inflate other devices and/or provide a gas directly to a patient (e.g., in pneumatic retinopexy) as desired.

In many embodiments, the system may comprise an inflatable occlusive element. The occlusive element may comprise any of the balloons, membranes, or expandable elements (e.g., mesh braid) described herein, in PCT/US2014/072302, in PCT/US2017/031153, and/or in U.S. Provisional Patent Application No. 62/688,233, filed Jun. 21, 2018. The occlusive element may, for example, be an inflatable balloon having at least two balloon chambers. The occlusive element may be disposed on or around a proximal portion of a catheter. The occlusive element may for example be advanced into an abdominal aorta and positioned adjacent renal ostia in a collapsed configuration. The occlusive element may then be expanded (e.g., inflated) by any of the inflation devices described herein into an expanded configuration which is sized to partially or fully occlude or divert blood flow from the renal artery ostia while allowing blood flow over the catheter shaft. It will be understood by one of ordinary skill in the art that any of the occlusive elements (e.g., balloons, etc.) described herein or any of the features thereof may be combined as desired in order to arrive at a system for treating or preventing AKI. Any of the occlusive elements, or any combination thereof, may be combined with any of the position indication means or features, flow disturbing means or elements, flow pumps, sensors, flow augmentation means or elements, injection synchronizer, fluid balancer, time-delayed release mechanism, any other element described herein, in PCT/US2014/072302, in PCT/US2017/031153, and/or in U.S. Provisional Patent Application No. 62/688,233, filed Jun. 21, 2018, or any combination thereof, as desired by one of ordinary skill in the art, to arrive at a system for treating or preventing AKI.

Figure 2:
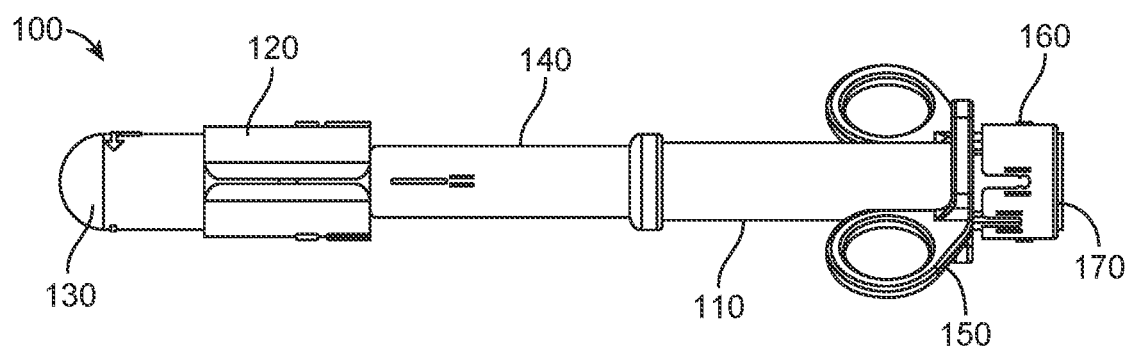
FIG. 2 shows a side view of the inflation device of FIG. 1, according to many embodiments.
Figure 3:
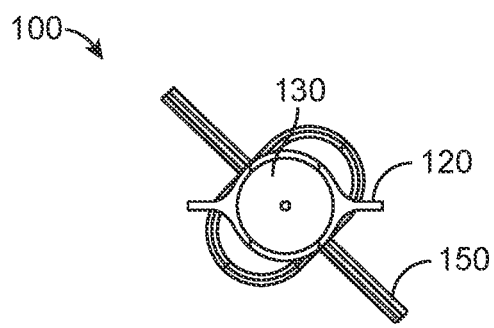
FIG. 3 shows a bottom view of the inflation device of FIG. 1, according to many embodiments.
Figure 6:
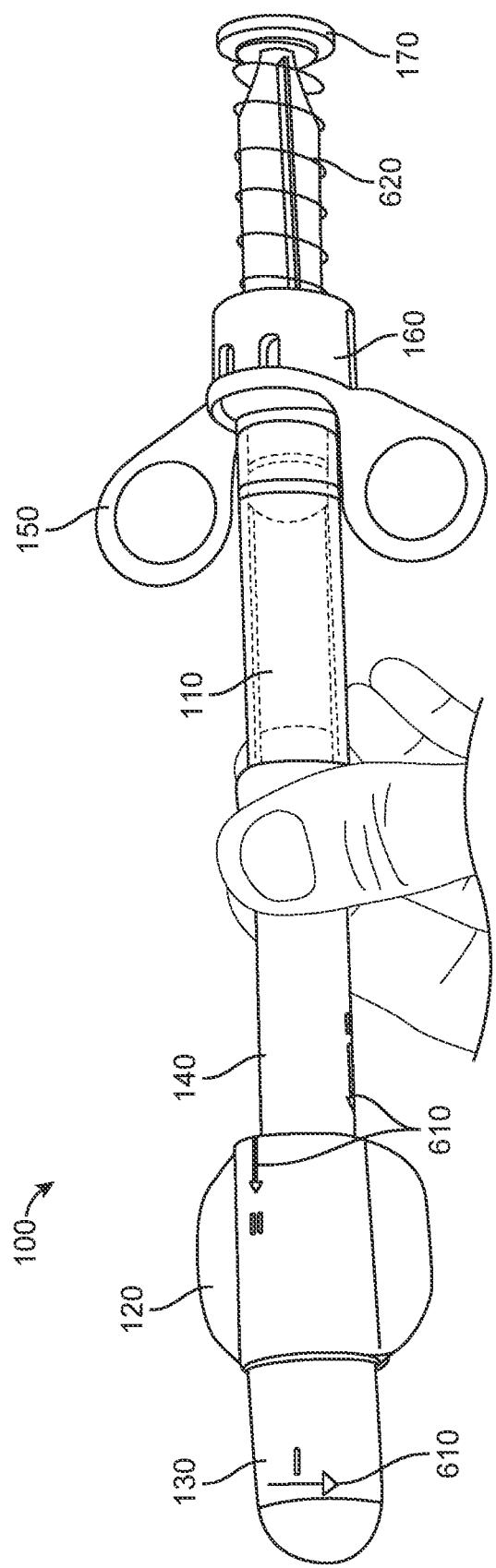
FIG. 6 shows an exemplary inflation device, according to many embodiments.

FIGS. 1-3 show various views of the external elements of an inflation device 100. FIG. 1 shows a perspective view of the inflation device 100. FIG. 2 shows a side view of the inflation device 100. FIG. 3 shows a bottom view of the inflation device 100. The inflation device 100 may comprise a housing 140. A syringe 110 comprising a plunger 170 slidably disposed therein may be disposed within the housing 140. The plunger 170 may comprise an unloaded position as shown here and a loaded position (as shown in FIG. 6) relative to the syringe 110. An optional safety cap 130 (also referred to herein as a protection cap) may be coupled to a distal end of the housing 140. The safety cap 130 may be removably coupled to the housing 140 as described herein. An optional stopper 160 may be disposed adjacent the plunger 170, for example coupled to a proximal end of the housing 140 and/or syringe 110. The stopper 160 may be configured to prevent the plunger 170 from moving past the loaded position when the gas is loaded into the syringe 110. An optional handle 150 may be coupled to the housing 140 and/or the syringe 110. The handle 150 may be used to provide the user a grip to aid in depression of the plunger 170 from the loaded position towards the unloaded position into a depressed position, for example to inflate a balloon of a balloon catheter as described herein. Optional rotation wings 120 may be coupled to the housing 140.

In some embodiments, the syringe 110 may be directly coupled to the housing 140. In some embodiments, the syringe 110 may be operably coupled to the housing 140. In some embodiments, the syringe 110 may be partially disposed within the housing 140. In some embodiments, the syringe 110 may be fully disposed within the housing 140.

In some embodiments, the syringe 110 may be an integral part of the inflation device. The syringe 110 may be reusable for multiple surgical procedures. Alternatively or in combination, the syringe 110 may be removable and may be replaceable after loading and use in a surgical procedure.

In some embodiments, the syringe 110 may be configured to be removed after loading by the inflation device and used coupled directly to a balloon catheter for use as a separate inflation device.

In some embodiments, the stopper 160 may be may be adjustable so as to set the loaded position of the plunger 170 to a predetermined volume. The predetermined volume may for example be determined based on a vasculature size of a patient and/or inflation volume of a balloon catheter.

The inflation device 100 may optionally comprise guide markings thereon (as shown in FIGS. 6-8F) which may be visible to the user and act to guide the user through the steps of loading the syringe 110 with the compressed gas and/or injecting the gas from the syringe 110 (e.g., into an attached balloon catheter as described herein).

Figure 4:
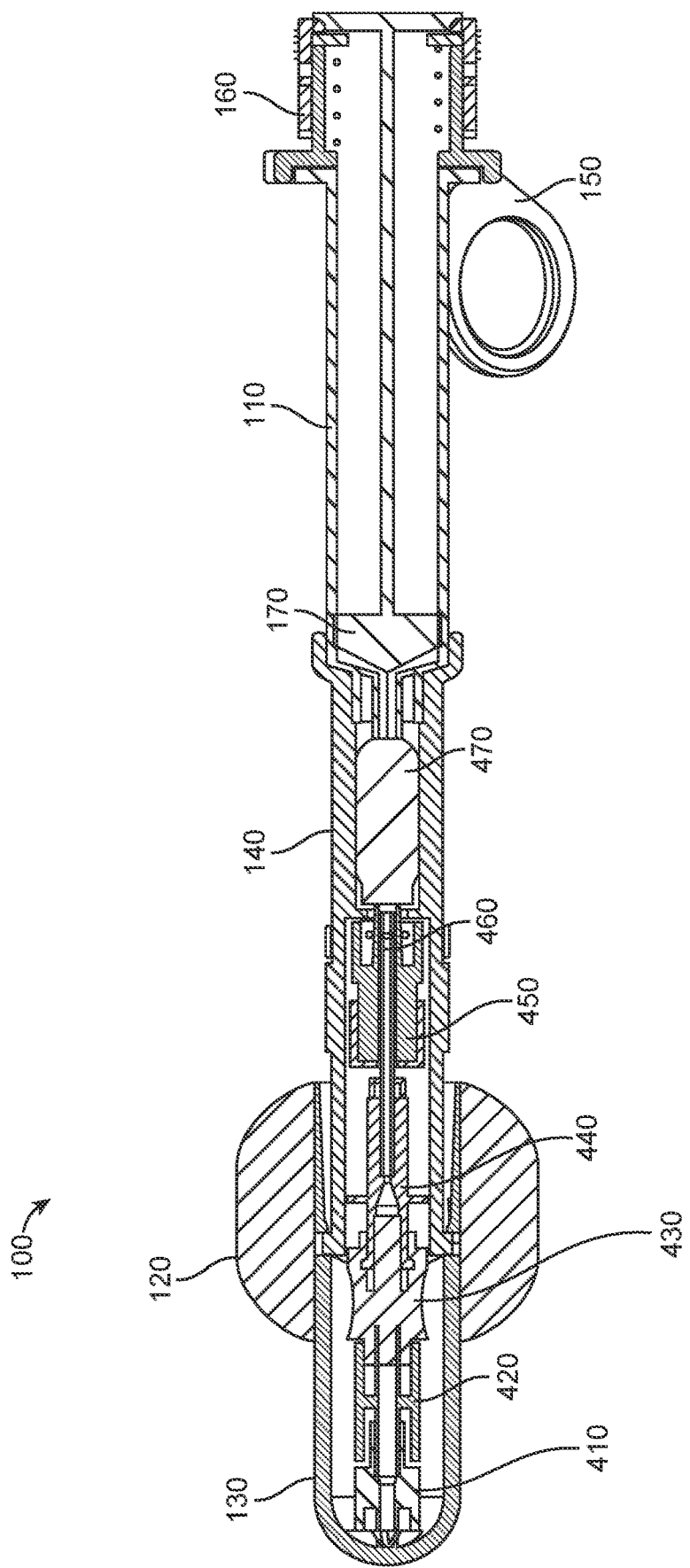
FIG. 4 shows a cross-sectional view of the inflation device of FIG. 1, according to many embodiments.

FIG. 4 shows a cross-sectional view of the inflation device 100 of FIGS. 1-3. The inflation device 100 may comprise a compressed gas canister 470 disposed within the housing 140. The compressed gas canister 470 may contain a gas. A puncture mechanism may be disposed within the housing 140. The puncture mechanism may be configured to open a fluid path between the compressed gas canister 470 and the syringe 110 in order to load the syringe 110 with the gas as described herein. The puncture mechanism may, for example, comprise a needle or pin. The inflation device 100 may also comprise a positive pressure mechanism 430 disposed within the housing 140 and operably coupled to the syringe 110. The positive pressure mechanism 430 may be configured to maintain the gas within the syringe 110 at a positive pressure relative to ambient pressure in order to prevent air from entering the syringe 110 after loading. The positive pressure mechanism 430 may optionally be coupled to a Tuohy valve 440 and silicone seal.

In some embodiments, the compressed gas canister 470 may be refillable. Alternatively or in combination, the compressed gas canister 470 may be removable. Alternatively or in combination, the compressed gas canister 470 may be replaceable. Removal and replacement of the gas canister 470, and/or refilling of the gas canister 470, may enable the device 100 to be a multi-use device.

The compressed gas canister 470 may contain a gas. The gas may comprise carbon dioxide. In at least some instances, the gas may be pure carbon dioxide.

The device 100 may comprise an outlet port in a distal tip of the housing 140, the outlet port being fluidly coupled to the syringe 110. The distal tip may be configured to be coupled to a catheter such that depression of the plunger 170 from the loaded position towards the unloaded position causes at least a portion of the gas loaded in the syringe 110 to be injected into the catheter via the outlet port.

In some embodiments, the optional safety cap 130 may be disposed around the distal tip and coupled to the housing 140. The safety cap 130 may be configured to prevent exposure of the distal tip (and subsequent coupling of the tip to a catheter) before the syringe 110 has been loaded with the gas.

The inflation device 100 may be used to load and maintain a syringe 110 with a gas at positive pressure just before a surgical procedure, such as inflation of a balloon catheter. The inflation device 100 may be configured to maintain the gas at a positive pressure prior to unloading.

In some embodiments, the distal tip may comprise the positive pressure mechanism 430.

The inflation device 100 may optionally comprise a pressure release mechanism (also referred to herein as a pressure relief mechanism 410). The pressure release mechanism may be coupled to the distal tip. Alternatively or in combination, the pressure release mechanism may be fluidly coupled to the syringe 110. The pressure release mechanism may be configured to release gas from the device 100. For example, in some embodiments the compressed gas cartridge may be configured to hold a first volume of gas that is greater than a second volume of gas which is loaded into the syringe 110. The pressure relief mechanism 410 may be configured to release excess gas after the puncture mechanism is engaged and the syringe 110 is loaded with the second volume of gas.

The inflation device 100 may comprise a one-way fitting 420. The one-way fitting 420 may be coupled to the distal tip. The one-way fitting 420 may be removably coupled to the distal tip of the device 100. In some embodiments, the one-way fitting 420 may be configured to prevent the distal tip from being coupled to the catheter. In some embodiments, the one-way fitting 420 may be configured to be removed to expose the distal tip only when the plunger 170 is in the loaded position and/or after the syringe 110 has been loaded.

In some embodiments, the one-way fitting 420 may be coupled to the distal tip and the pressure release mechanism such that removal to the pressure release mechanism-one-way fitting 420 "cup" exposes the distal tip, for example to allow the distal tip to be coupled to a catheter as described herein.

In some embodiments, the optional safety cap 130 may be disposed around the one-way and coupled to the housing 140. The safety cap 130 may be configured to prevent removal of the one-way fitting 420 when the syringe 110 is in the first position and allow removal of the one-way fitting 420 when the syringe 110 is in the second position.

The rotation wings 120 may comprise an actuation mechanism and may be used to engage (and/or prevent accidental engagement of) the puncture mechanism and bring the compressed gas canister 470 into fluid communication with the syringe 110. The rotation wings 120 may for example have a first wing position and a second wing position.

In some embodiments, actuation of the rotation wings 120 from the first wing position to the second wing position may actuate the syringe 110 from a first position to a second position relative to the puncture mechanism within the housing 140, in order to engage (and/or prevent accidental engagement of) the puncture mechanism and bring the compressed gas canister 470 into fluid communication with the syringe 110. For example, rotating the rotation wings 120 may actuate the syringe 110 from a first rotational position relative to the housing 140 to a second rotational position relative to the housing 140. Alternatively or in combination, rotating the rotation wings 120 may actuate the syringe 110 from a first longitudinal position relative to the housing 140 to a second longitudinal position relative to the housing 140.

In some embodiments, actuation of the rotation wings 120 from the first wing position to the second wing position may actuate the compressed gas canister 470 from a first position to a second position relative to the puncture mechanism within the housing 140, in order to engage (and/or prevent accidental engagement of) the puncture mechanism and bring the compressed gas canister 470 into fluid communication with the syringe 110. For example, rotating the rotation wings 120 may actuate the gas canister 470 from a first rotational position relative to the housing 140 to a second rotational position relative to the housing 140. Alternatively or in combination, rotating the rotation wings 120 may actuate the gas canister 470 from a first longitudinal position relative to the housing 140 to a second longitudinal position relative to the housing 140.

In some embodiments, actuation of the rotation wings 120 from the first wing position to the second wing position may actuate the puncture mechanism from a first position to a second position relative to the gas canister 470 within the housing 140, in order to engage (and/or prevent accidental engagement of) the puncture mechanism and bring the compressed gas canister 470 into fluid communication with the syringe 110. For example, rotating the rotation wings 120 may actuate the puncture mechanism from a first rotational position relative to the housing 140 to a second rotational position relative to the housing 140. Alternatively or in combination, rotating the rotation wings 120 may actuate the puncture mechanism from a first longitudinal position relative to the housing 140 to a second longitudinal position relative to the housing 140.

Alternatively or in combination, the handle 150 may comprise an actuation mechanism and may be used to engage (and/or prevent accidental engagement of) the puncture mechanism and bring the compressed gas canister 470 into fluid communication with the syringe 110. The handle 150 may, for example, have a first handle position and a second handle position.

In some embodiments, actuation of the handle 150 from the first handle position to the second handle position may actuate the syringe 110 from a first position to a second position relative to the puncture mechanism within the housing 140, in order to engage (and/or prevent accidental engagement of) the puncture mechanism and bring the compressed gas canister 470 into fluid communication with the syringe 110. For example, rotating the handle 150 may actuate the syringe 110 from a first rotational position relative to the housing 140 to a second rotational position relative to the housing 140. Alternatively or in combination, rotating the handle 150 may actuate the syringe 110 from a first longitudinal position relative to the housing 140 to a second longitudinal position relative to the housing 140.

In some embodiments, actuation of the handle 150 from the first handle position to the second handle position may actuate the compressed gas canister 470 from a first position to a second position relative to the puncture mechanism within the housing 140, in order to engage (and/or prevent accidental engagement of) the puncture mechanism and bring the compressed gas canister 470 into fluid communication with the syringe 110. For example, rotating the handle 150 may actuate the gas canister 470 from a first rotational position relative to the housing 140 to a second rotational position relative to the housing 140. Alternatively or in combination, rotating the handle 150 may actuate the gas canister 470 from a first longitudinal position relative to the housing 140 to a second longitudinal position relative to the housing 140.

In some embodiments, actuation of the handle 150 from the first handle 150 position to the second handle 150 position may actuate the puncture mechanism from a first position to a second position relative to the gas canister 470 within the housing 140, in order to engage (and/or prevent accidental engagement of) the puncture mechanism and bring the compressed gas canister 470 into fluid communication with the syringe 110. For example, rotating the handle 150 may actuate the puncture mechanism from a first rotational position relative to the housing 140 to a second rotational position relative to the housing 140. Alternatively or in combination, rotating the handle 150 may actuate the puncture mechanism from a first longitudinal position relative to the housing 140 to a second longitudinal position relative to the housing 140.

Figure 5:
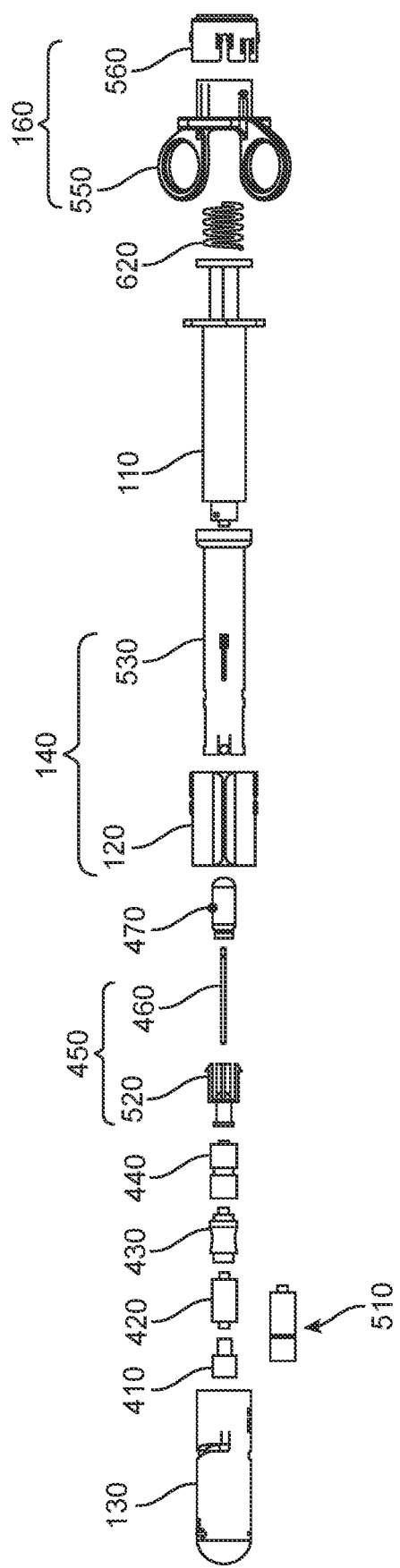
FIG. 5 shows an exploded view of the inflation device of FIG. 1, according to many embodiments.

FIG. 5 shows an exploded view of the inflation device 100 of FIGS. 1-4.

The housing 140 may comprise a cartridge enclosure 530. The housing 140 may optionally comprise one or more rotation wings 120.

The distal tip may comprise a catheter fitting. The catheter fitting may be a custom female connector configured to prevent coupling of the distal tip to an intravenous line. Alternatively or in combination, the catheter fitting may comprise a male swabable connector preventing air from entering the catheter and allowing $CO_2$ gas from inflator (equipped with pusher rod female swabable Luer, like the "C1000 Clave Connector" sold by ICU Medical, Inc. of San Clemente, Calif.) to flow in and out of catheter only when Inflator and catheter lines are connected.

The puncture mechanism may comprise a piercing needle 460 and a piercing needle adaptor 520 as shown. Alternatively or in combination, the puncture mechanism may comprise a straight tip hypotube with a sharp or square edge The positive pressure mechanism 430 may comprise a positive pressure valve. Alternatively or in combination, the positive pressure mechanism 430 may comprise a one-way valve. Alternatively or in combination, the positive pressure mechanism 430 may comprise a duck valve.

The pressure relief mechanism 410 may comprise a pressure relief duck valve. Alternatively or in combination, the pressure relief mechanism 410 may comprise a spring loaded plunger 170 made of rubber plastic.

The one-way fitting 420 may comprise a male-male connector. Alternatively or in combination, the one-way fitting 420 may comprise a male-female connector.

The pressure relief mechanism 410 and one-way fitting 420 may together comprise a removable cup coupled to the distal tip (e.g., the positive pressure mechanism 430 as shown in FIG. 5).

The stopper 160 may comprise an inflation limiting base 550 and an inflation limiting ring 560. Alternatively or in combination, the stopper 160 may comprise a plunger retaining spring 620 (which may optionally also act as a time-delayed release mechanism as described herein). Alternatively or in combination, the stopper 160 may comprise a rotational ring with several length grooves complying with a protruded tenon that acts like a stopper at different length groves on the ring.

Any of the inflation devices 100 described herein may optionally comprise a time-delayed release mechanism configured to automatically collapse an inflatable balloon of a balloon catheter after a pre-determined amount of time following deployment (i.e., inflation). The time-delayed release mechanism may be provided on the handle 150, around the plunger 170, on a controller of the inflation device 100, or otherwise operably coupled to the plunger 170. The time-delayed release mechanism may be operably coupled to the plunger 170. The time-delayed release mechanism may be configured to actuate the plunger 170 from a depressed position to the loaded position after a pre-determined amount of time following depression of the plunger 170. The depressed position may be the unloaded position.

For example, the inflation device 100 may comprise a time-delayed release mechanism configured to automatically collapse a balloon fluidly coupled thereto after a pre-determined amount of time following deployment. The time-delayed release mechanism may, for example, comprise an energy accumulation and storage component and a time-delay component. For example, the time-delayed release mechanism may comprise a spring with a frictional damper, examples of which are shown in FIGS. 5, 6, 9 and 10A-10L. The energy accumulation and storage component may, for example, be a spring or spring-coil or the like. The time-delayed release mechanism may, for example, be adjustable by one or more of the user, the manufacturer, or both. The time-delayed release mechanism may further comprise a synchronization component, for example to synchronize the injection of a contrast media or other harmful agent with the opening or closing of the balloon catheter. For example, injection may be synchronized with occlusion of the renal arteries by an inflatable balloon such that a contrast media may be prevented from entering the renal arteries.

Figure 9:
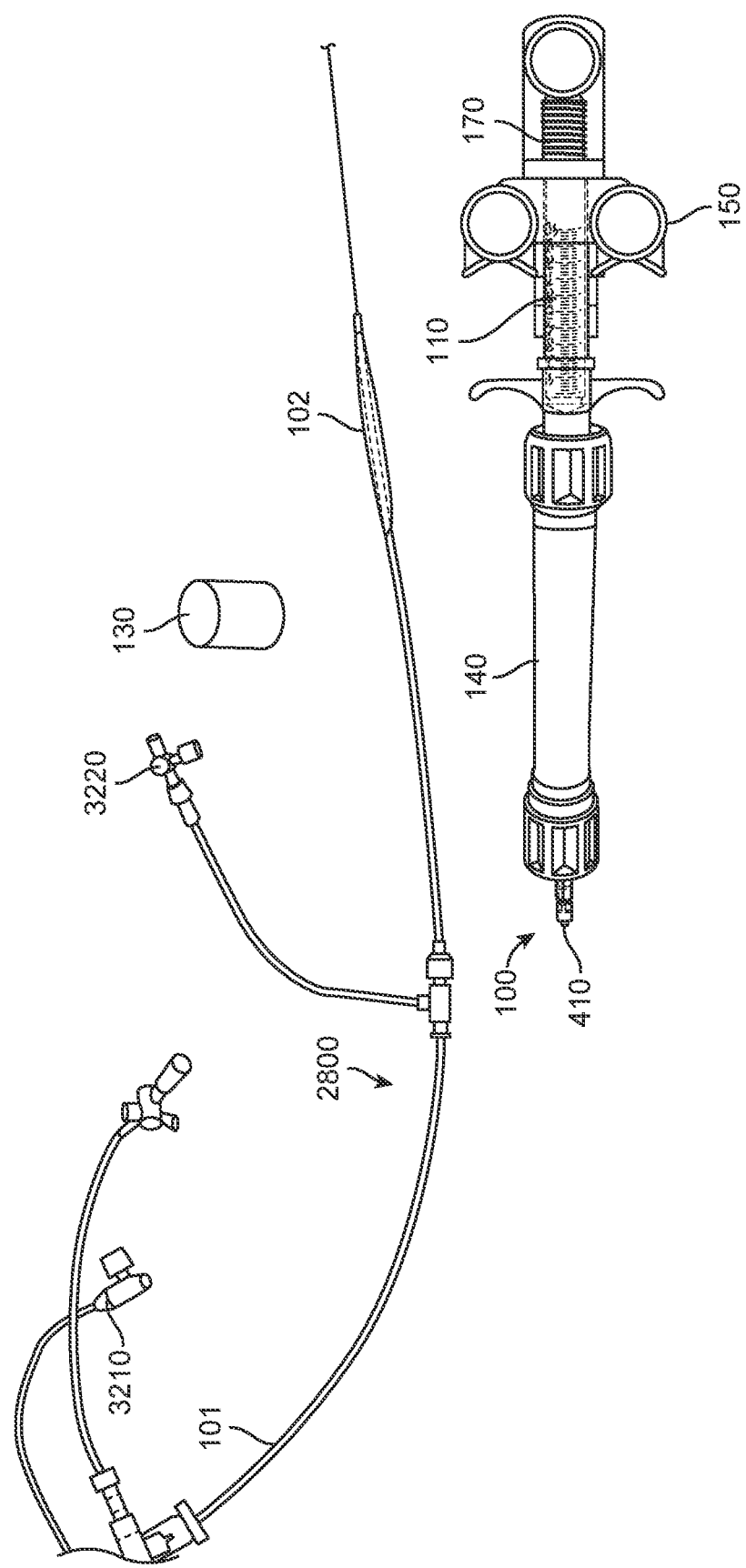
FIG. 9 shows yet another exemplary inflation device, according to many embodiments.

The time-delayed release mechanism may, for example, comprise a spring disposed around a syringe plunger 170 of syringe 110 of the inflation device 100. The distal tip of the inflation device 100 may be configured to attach to the distal end of the catheter device (as shown in FIG. 9), for example, via a press-fit, screw-fit, or Luer-lock connector, or any of the fittings described herein. The user may grip the handle 150 while depressing the syringe pump (also referred to herein as a plunger 170) and attached spring into the syringe 110 to expand the inflatable balloon (as shown in FIGS. 10K-10L). Actuation of the syringe pump from a loaded position towards an unloaded position may, in the case of a balloon catheter, for example, inject a gas into the balloon(s) via an outlet port in the distal tip to the catheter device in order to inflate and expand the balloon. Removal of the pressure applied to the syringe pump may cause the spring to release the energy it accumulated by being depressed and quickly retract the syringe pump from its depressed position (for example, the fully unloaded position) within the syringe 110 to deflate and collapse the balloon after a pre-determined amount of time. The time-delayed release mechanism may further comprise a frictional damper configured to introduce the pre-determined amount of time between the inflation of the balloon, release of the syringe pump, and the release of energy by the spring. It will be understood by one of ordinary skill in the art that the amount of friction applied by the damper to the syringe pump and/or spring may be calibrated to generate any pre-determined time-delay desired such as by providing the spring with various spring constants depending on the time-delay desired.

The time-delayed release mechanism may, for example, be adjustable by one or more of the user, the manufacturer, or both. The time-delayed release mechanism may further comprise a synchronization component to synchronize the injection of a contrast media or other harmful agent with the opening or closing of the balloon catheter shaft device as described herein. For example, injection may be synchronized with occlusion of the renal arteries by the balloon such that a contrast media may be prevented from entering the renal arteries.

In some embodiments, one or more of the elements described herein may comprise polycarbonate. For example, the syringe 110, the pressure relief duck valve, the one-way male-male connector, the positive pressure valve 430, and/or the Tuohy valve 440 may comprise polycarbonate.

In some embodiments, one or more of the elements described herein may comprise nylon. For example, the safety cap 130, the piercing needle adapter, the housing 140, the rotation wings 120, the cartridge enclosure 530, the stopper 160, the inflation limiting base 550, and/or the inflation limiting ring 560 may comprise nylon.

In some embodiments, one or more of the elements described herein may comprise metal. For example, the piercing needles, the compressed gas canister 470, and/or the plunger 170 retaining spring may comprise metal.

In some embodiments, one or more of the elements described herein may comprise silicone. For example, the Tuohy valve 440 may comprise or be coupled to a silicone seal.

The male swabable Luer may comprise a metal plunger 170 with a silicone rubber seal (O-Ring) that travels inside a plastic housing 140 and pressure activated against a metal spring.

The inflation device may comprise one or more optional safety features as described herein. The one or more optional safety features may be useful in preventing accidental discharge of the compressed gas into the device prior to the intended time of use, preventing ejection of the plunger 170 from the syringe 110 during loading with the compressed gas and/or while the device is holding the gas at positive pressure, preventing accidental discharge of the gas into a catheter prior to correct insertion into a patient, and/or preventing accidental discharge of the gas into a line other than the procedural catheter (e.g., into a patient's intravenous line). It will be understood by one of ordinary skill in the art that any number and/or combination of safety features may be used in the inflation device as desired for a particular use and/or user.

The inflation device may optionally comprise a positive pressure mechanism 430 configured to maintain the gas within the syringe 110 at a positive pressure relative to ambient pressure in order to prevent air from entering the syringe 110 after loading. The positive pressure mechanism 430 may comprise a positive pressure valve for example. By preventing air from entering the closed system, the positive pressure mechanism 430 may ensure that the gas delivered from the device (e.g., to a balloon catheter) remains pure. For example, pure carbon dioxide is known to readily dissolve in the blood while air may remain in the blood as emboli which may be harmful to the patient. Thus, ensuring that no air can enter the system may prevent the formation of air emboli in the event of accidental injection or leakage of the inflation gas (e.g., carbon dioxide) into the blood stream during use.

The inflation device may optionally comprise an actuation mechanism to move the syringe 110 from a first position to a second position relative to the puncture mechanism, in order to engage (and/or prevent accidental engagement of) the puncture mechanism and bring the compressed gas canister 470 into fluid communication with the syringe 110, for example. The actuation mechanism may, for example, comprise a rotatable threaded cap which may be rotated from a first rotational position relative to the housing 140 to a second rotation position relative to the housing 140 in order to rotate the syringe 110 relative to the puncture mechanism (i.e., rotate the puncture mechanism relative to the syringe 110). The actuation mechanism may for example be coupled to the housing 140 or optional rotation wings 120 in order to allow the user to actuate (e.g., rotate) the actuation mechanism as described herein.

The inflation device may optionally comprise an actuation mechanism to move the gas canister 470 from a first position to a second position relative to the puncture mechanism, in order to engage (and/or prevent accidental engagement of) the puncture mechanism and bring the compressed gas canister 470 into fluid communication with the syringe 110, for example. The actuation mechanism may, for example, comprise a rotatable threaded cap which may be rotated from a first rotational position relative to the housing 140 to a second rotation position relative to the housing 140 in order to rotate the gas canister 470 relative to the puncture mechanism (i.e., rotate the puncture mechanism relative to the gas canister 470).

It will be understood by one of ordinary skill in the art that any of the elements described herein may be combined with any other element, or combination of elements, described herein. For example, in some embodiments the inflation device may comprise a housing 140, a compressed gas canister 470 disposed within the housing 140, a syringe 110 comprising a plunger 170 slidably disposed therein, a puncture mechanism, and a positive pressure mechanism 430 as described herein. In some embodiments, the inflation device may comprise a housing 140, a compressed gas canister 470 disposed within the housing 140, a syringe 110 comprising a plunger 170 slidably disposed therein, a puncture mechanism, and an outlet port in a distal tip of the housing 140, the outlet port being fluidly coupled to the syringe 110, as described herein. In some embodiments, the inflation device may comprise a housing 140, a compressed gas canister 470 disposed within the housing 140, a syringe 110 comprising a plunger 170 slidably disposed therein, a puncture mechanism, a positive pressure mechanism 430, and an outlet port in a distal tip of the housing 140, the outlet port being fluidly coupled to the syringe 110, as described herein.

FIG. 6 shows an exemplary inflation device 100. The inflation device 100 may comprise a compressed gas canister 470 disposed within a housing 140 and containing a gas, for example, pure carbon dioxide, as described herein. A syringe 110 comprising a plunger 170 slidably disposed therein may be at least partially disposed within the housing 140 as described herein. A puncture mechanism may be disposed within the housing 140. The puncture mechanism may be configured to open a fluid path between the compressed gas canister 470 and the syringe 110 as described herein. The inflation device 100 may also comprise a positive pressure mechanism 430 disposed within the housing 140 and operably coupled to the syringe 110 as described herein. The inflation device 100 may further comprise a handle 150 and rotation wings 120 coupled to the housing 140 as described herein. The inflation device 100 may comprise a safety cap 130 coupled to the housing 140 as described herein. The inflation device 100 may comprise a pressure release mechanism and/or one-way fitting 420 coupled to a distal end of the housing 140 as described herein. The inflation device 100 may comprise a stopper 160 adjacent the plunger 170. The inflation device 100 may further comprise a time-delayed release mechanism (e.g., a spring) coupled to the syringe 110 plunger 170 as described herein. The device 100 may also comprise one or more visual guide markings 610 to guide the user through the steps of loading the syringe 110 with the compressed gas and/or injecting the gas from the syringe 110 (e.g., into an attached balloon catheter) as described herein.

Figure 7:
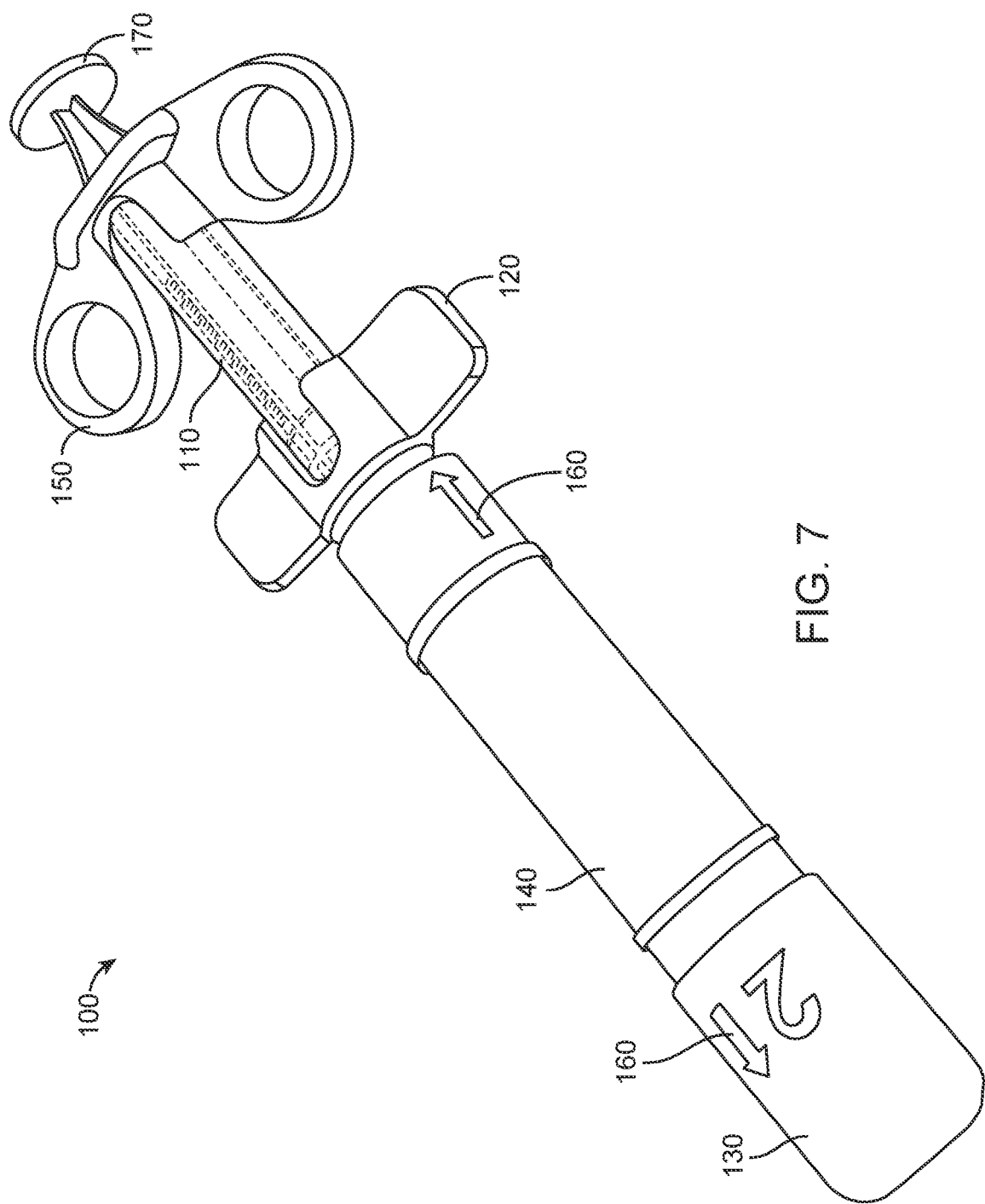
FIG. 7 shows another exemplary inflation device, according to many embodiments.

FIG. 7 shows another exemplary inflation device 100. The inflation device 100 may comprise a compressed gas canister 470 disposed within a housing 140 and containing a gas, for example pure carbon dioxide, as described herein. A syringe 110 comprising a plunger 170 slidably disposed therein may be at least partially disposed within the housing 140 as described herein. A puncture mechanism may be disposed within the housing 140. The puncture mechanism may be configured to open a fluid path between the compressed gas canister 470 and the syringe 110 as described herein. The inflation device 100 may also comprise a positive pressure mechanism 430 disposed within the housing 140 and operably coupled to the syringe 110 as described herein. The inflation device 100 may further comprise a handle 150 and rotation wings 120 coupled to the housing 140 as described herein. The inflation device 100 may comprise a safety cap 130 coupled to the housing 140 as described herein. The inflation device 100 may comprise a pressure release mechanism and/or one-way fitting 420 coupled to a distal end of the housing 140 as described herein. In at least some instances, the device 100 may also comprise one or more visual guide markings 610 to guide the user through the steps of loading the syringe 110 with the compressed gas and/or injecting the gas from the syringe 110 (e.g. into an attached balloon catheter) as described herein.

Figure 8A:
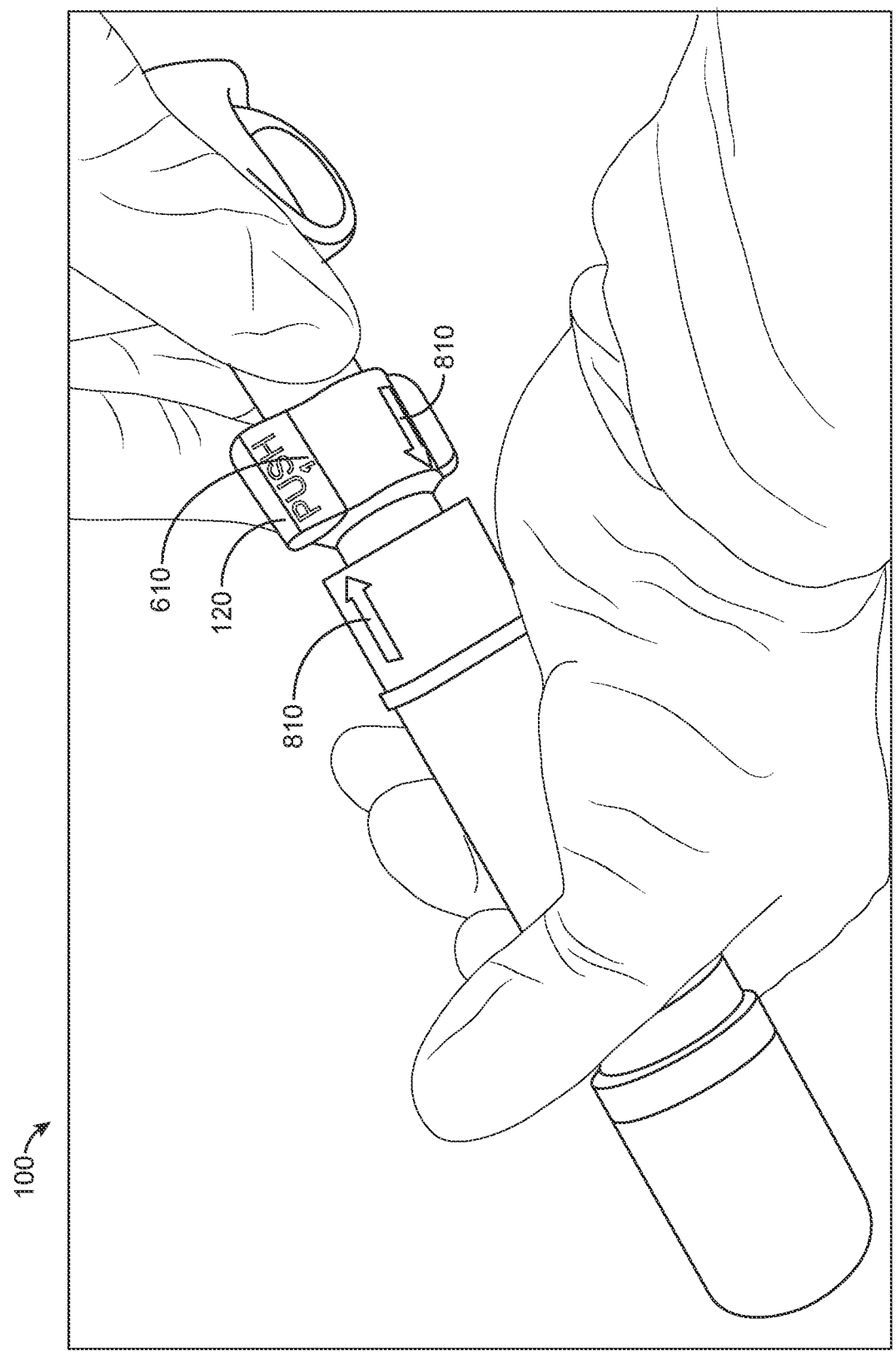
FIGS. 8A-8F show various steps involved in loading and preparing the inflation device of FIG. 7 for use, according to many embodiments.
Figure 8B:
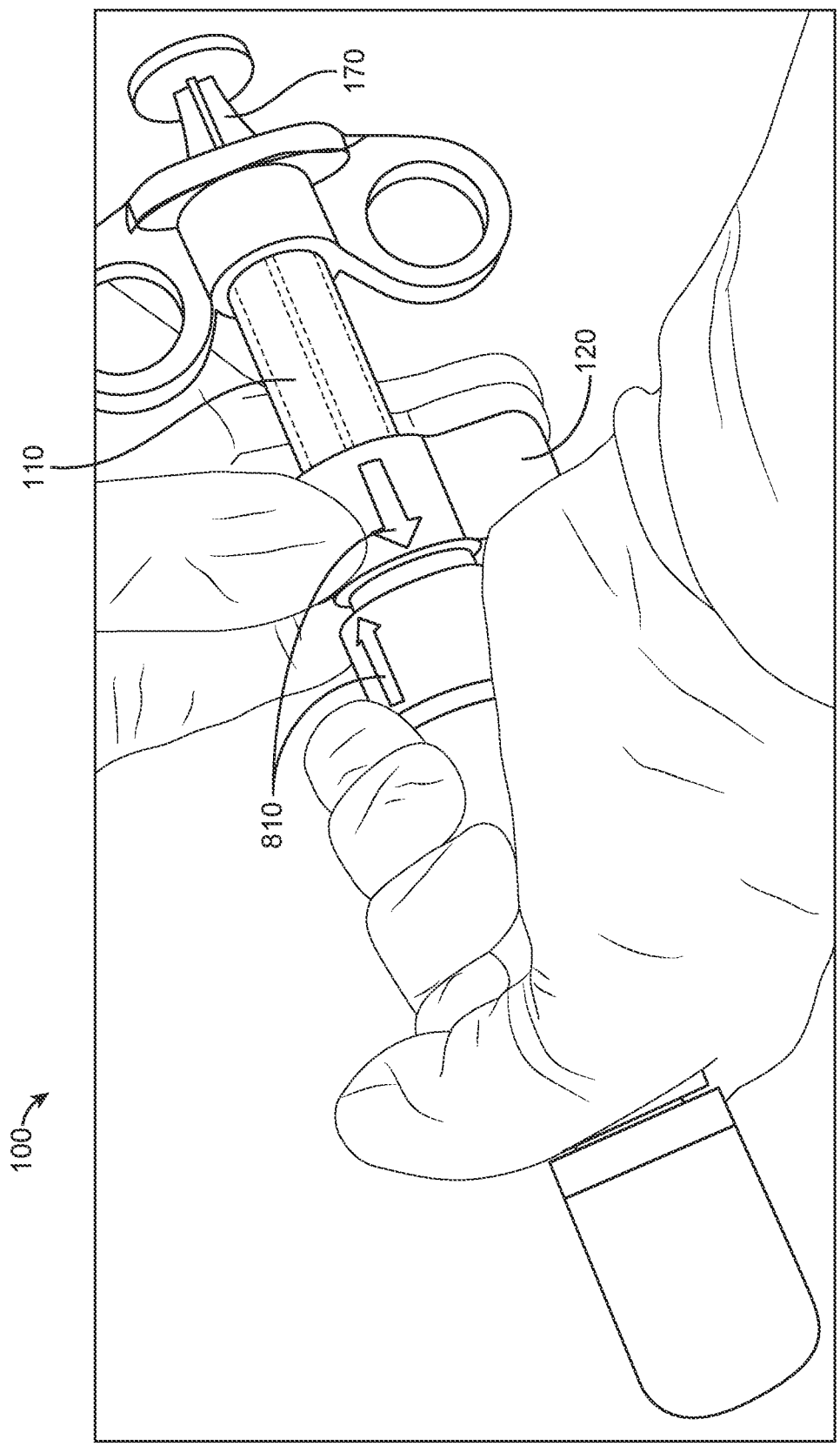
Figure 8C:
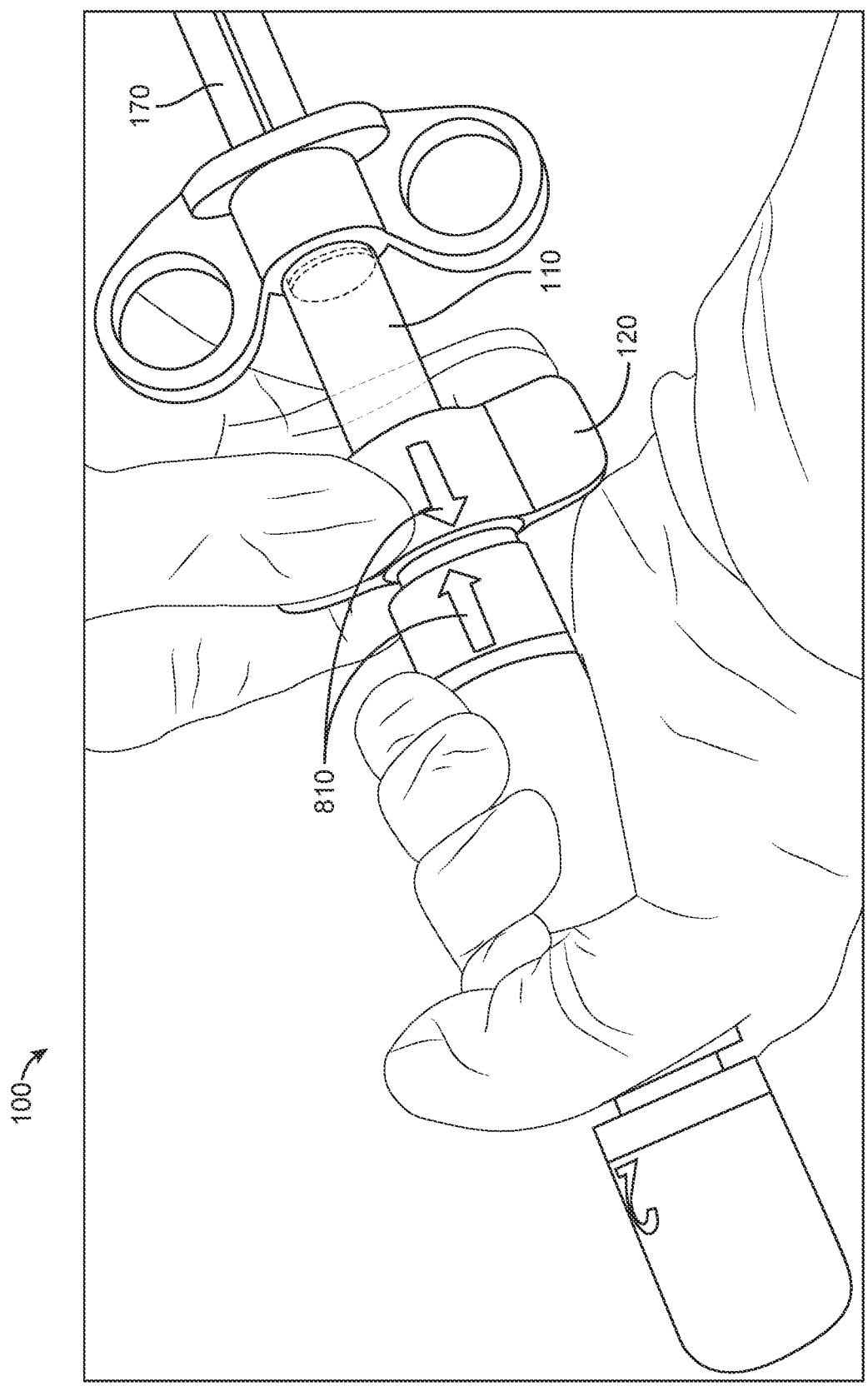
Figure 8D:
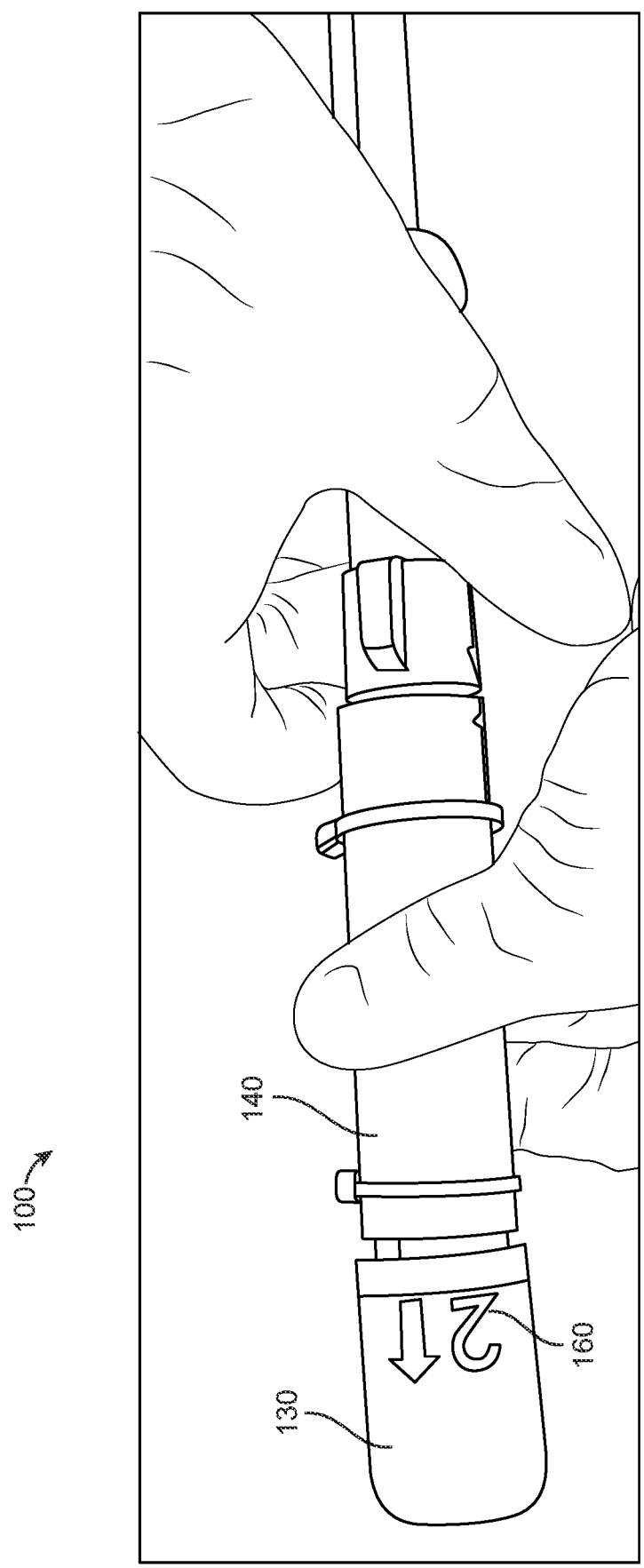
Figure 8E:
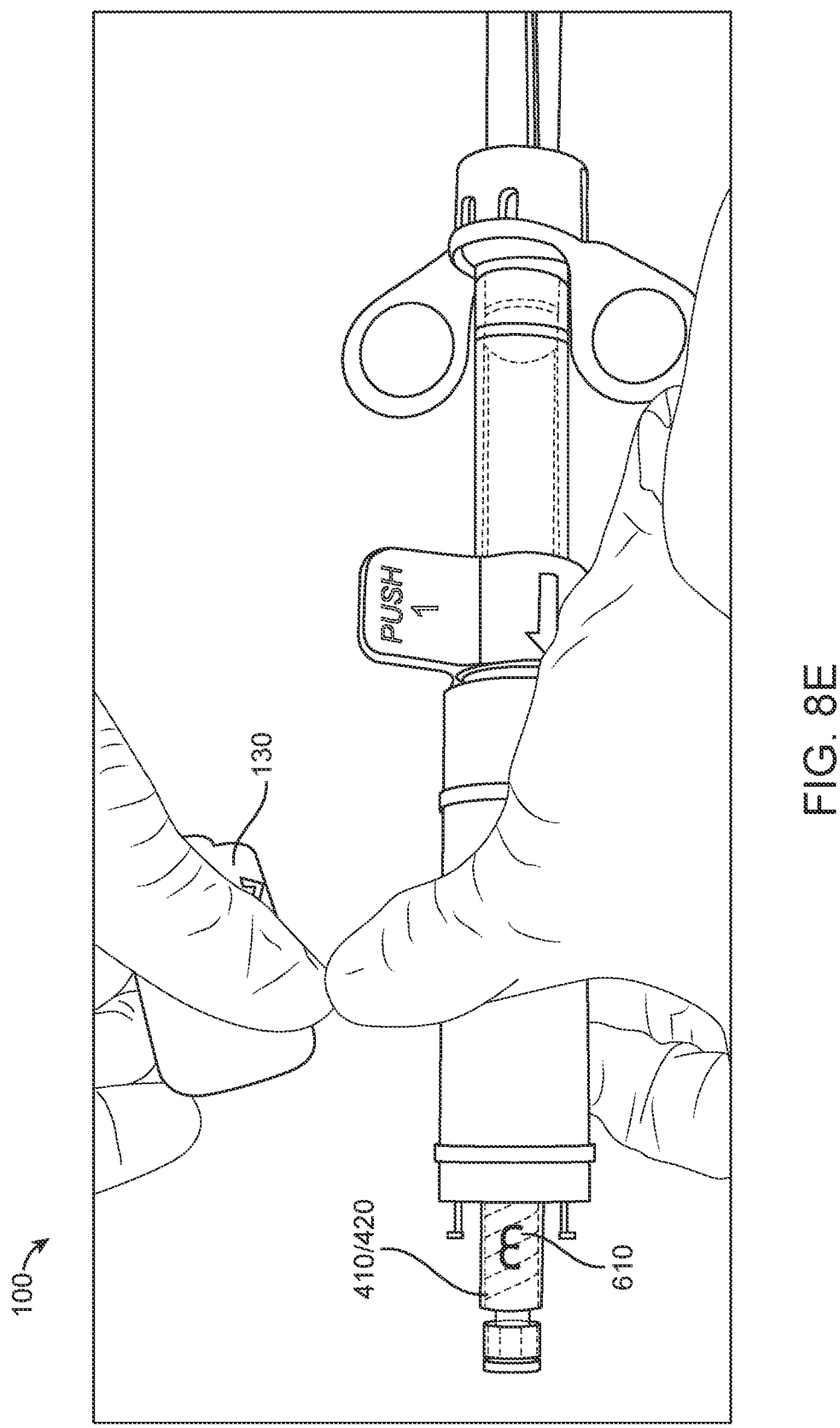
Figure 8F:
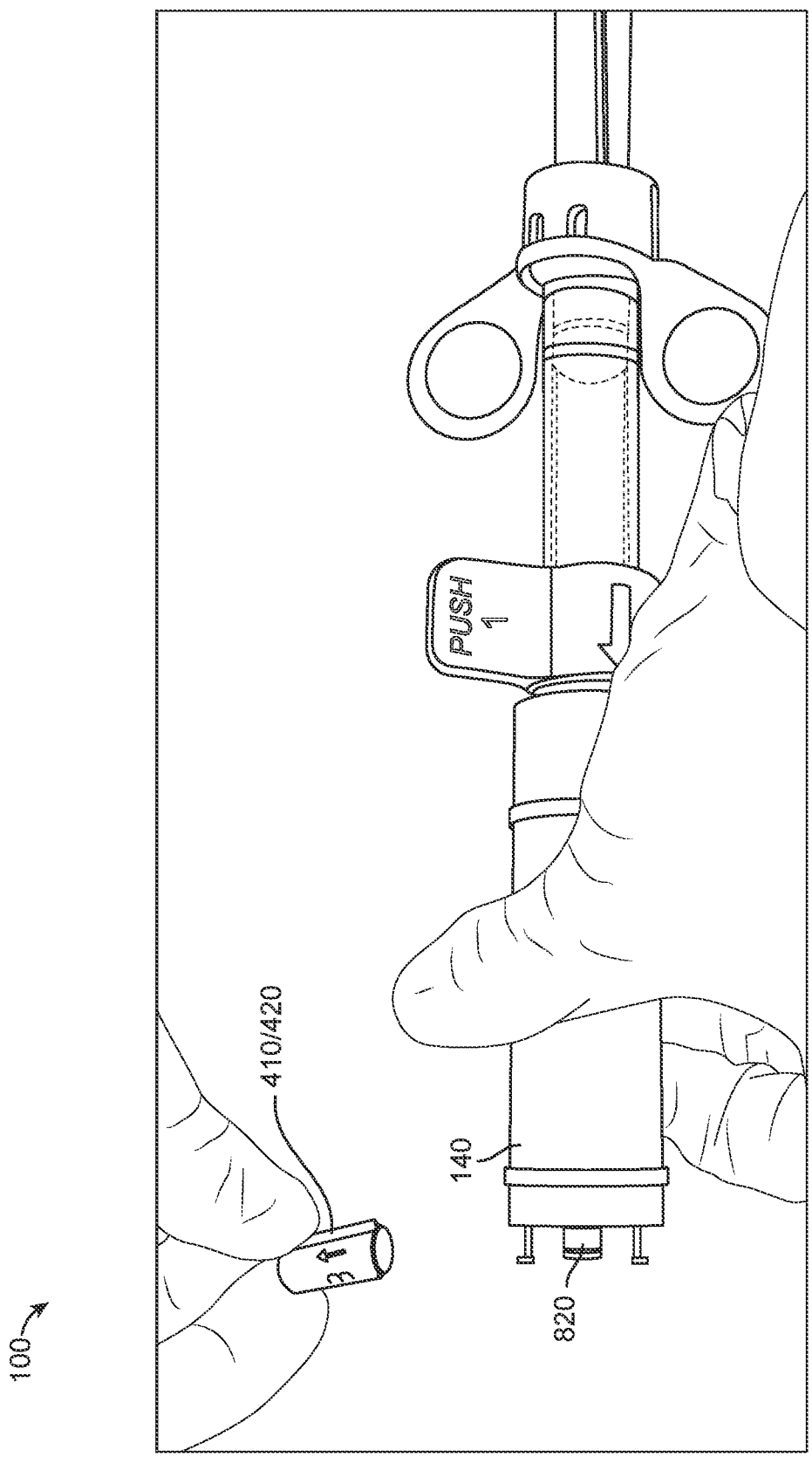

FIGS. 8A-8F show various steps involved in loading and preparing the inflation device of FIG. 7 for use. FIGS. 8A-8C show the first step of puncturing the compressed gas canister 470 and loading the syringe 110 with gas. FIGS. 8D-8E show removal of the safety cap 130 by the user. FIG. 8F shows removal of the one-way fitting 420 by the user.

FIG. 8A shows the inflation device 100 prior to use. The device 100 may comprise guide markings 610 on the rotation wings 120. The guide markings 610 may for example indicate the step order (i.e.g step 1, step 2, step 3, etc.) and/or the direction or mechanism of actuation (e.g. rotation, pushing, pulling or the like). Guide markings 610 may optionally take the form or guiding arrows. For example, the arrows shown in FIG. 8A are misaligned prior to use of the device 100. The guide markings 610 may indicate to the user that the first step in the use of the inflation device 100 is to rotate the rotation wings 120 so as to align the guide arrows 810.

FIG. 8B shows rotation of the rotation wings 120 by the user. The plunger 170 may be in an unloaded position prior to alignment of the guide arrows 810.

FIG. 8C shows the inflation device 100 after the guide arrows 810 have been aligned. Rotation of the rotation wings 120 may be configured to actuate (e.g., rotate) the syringe 110 from a first position to a second position relative to the puncture mechanism within the housing 140. Actuation of the syringe 110 from the first position to the second position may engage the puncture mechanism to put the syringe 110 into fluid communication with the compressed gas canister 470 such that the gas contained therein is loaded into the syringe 110 and the plunger 170 is moved from the unloaded position (FIG. 8B) and the loaded position (FIG. 8C). The handle 150 may act like a stopper 160 to prevent the plunger 170 from moving past the loaded position when the gas is loaded into the syringe 110.

FIG. 8D shows a protection cap coupled to the distal end of the housing 140. The protection cap may be disposed around a distal tip comprising an outlet port. The distal tip may be configured to be coupled to a catheter as described herein. The protection cap may comprise guide markings 610, for example, markings indicating to the user that removal of the protection cap by pulling is the second step in the use of the inflation device 100. The protection cap may be configured to prevent exposure of the distal tip, and thus prevent the ability of the user to couple the distal tip to a catheter, prior to loading of the syringe 110 by actuating the syringe 110 and engaging the puncture mechanism in the first step as shown in FIGS. 8A-8C. The protection cap may for example be fixedly coupled to the housing 140 until a release mechanism is engaged to enable removal of the cap and exposure of the distal tip. Rotation of the rotation wings 120 and actuation of the syringe 110 from the first position to the second position may for example bring the release mechanism of the protection cap into proper alignment to allow the protection cap to be removed from the housing 140.

FIG. 8E shows the protection cap removed and the distal tip exposed. The distal tip may optionally be coupled to a pressure relief mechanism 410 as described herein. The distal tip may optionally have a one-way fitting 420 coupled thereto as a further safety mechanism as described herein. The one-way fitting 420 may prevent the distal tip from being accidentally coupled to a catheter. The pressure relief mechanism 410 and/or one-way fitting 420 may comprise guide markings 610, for example, markings indicating that the third step in the use of the inflation device 100 is removal of the pressure relief mechanism 410 and/or one-way fitting 420 to allow the distal tip to be connected to a catheter as described herein.

FIG. 8F shows the pressure relief mechanism 410 and/or one-way fitting 420 removed and the distal tip 820 exposed and ready to be coupled to a balloon catheter for selectively inflating and deflating a balloon of the balloon catheter.

FIG. 9 shows yet another exemplary inflation device 100. The inflation device 100 may comprise a compressed gas canister 470 disposed within a housing 140 and containing a gas, for example pure carbon dioxide, as described herein. A syringe 110 comprising a plunger 170 slidably disposed therein may be at least partially disposed within the housing 140 as described herein. A puncture mechanism may be disposed within the housing 140. The puncture mechanism may be configured to open a fluid path between the compressed gas canister 470 and the syringe 110 as described herein. The inflation device 100 may also comprise a positive pressure mechanism 430 disposed within the housing 140 and operably coupled to the syringe 110 as described herein. The inflation device 100 may further comprise a handle 150 coupled to the housing 140 as described herein. The inflation device 100 may comprise a safety cap 130 coupled to the housing 140 as described herein. The inflation device 100 may comprise a pressure release mechanism and/or one-way fitting 420 coupled to a distal end of the housing 140 as described herein. The safety cap 130 is shown pre-removed from the housing 140 to highlight the function of pressure release mechanism (particularly in FIG. 10D) but would typically be disposed around the distal tip 820 prior to actuation of the puncture mechanism as described herein.

A system comprising the inflation device 100 may further comprise a balloon catheter device 2800. In some embodiments, the balloon catheter device may be used to occlude renal artery ostia of a patient or subject. The catheter device 2800 may comprise a catheter 101 with a first balloon chamber or first balloon 303a and a second balloon chamber or second balloon 303b on a proximal portion thereof. A distal portion 3200 of the catheter 101 may comprise a connection element 3210 configured to connect to the tip of the inflation device 100. The distal portion 3200 of the catheter 101 may be configured to remain external to the subject when the first and second balloon chambers 303a, 303b are positioned adjacent the renal arteries of the subject. The catheter 101 and the syringe 110 may be fluidly connected, for example, to allow a gas to pass from the syringe 110 to the catheter 101 and into the balloon chambers 303a, 303b via the outlet port of the inflation device and the catheter 101. Actuation of the plunger 170 from a loaded position towards an unloaded position may expand the balloon chambers 303a, 303b with the gas as described herein. The distal portion 3200 of the catheter 101 may comprise one or more infusion port 3220. The infusion port 3220 may, for example, be configured to infuse a medication or other fluid (e.g., normal saline) into the aorta, for example via a side aperture in the catheter 101.

It will be understood by one of ordinary skill in the art that any of the catheter devices described herein, or known to one of ordinary skill in the art, may be attached to the inflation device 100 in a similar manner as described herein.

Figure 10A:
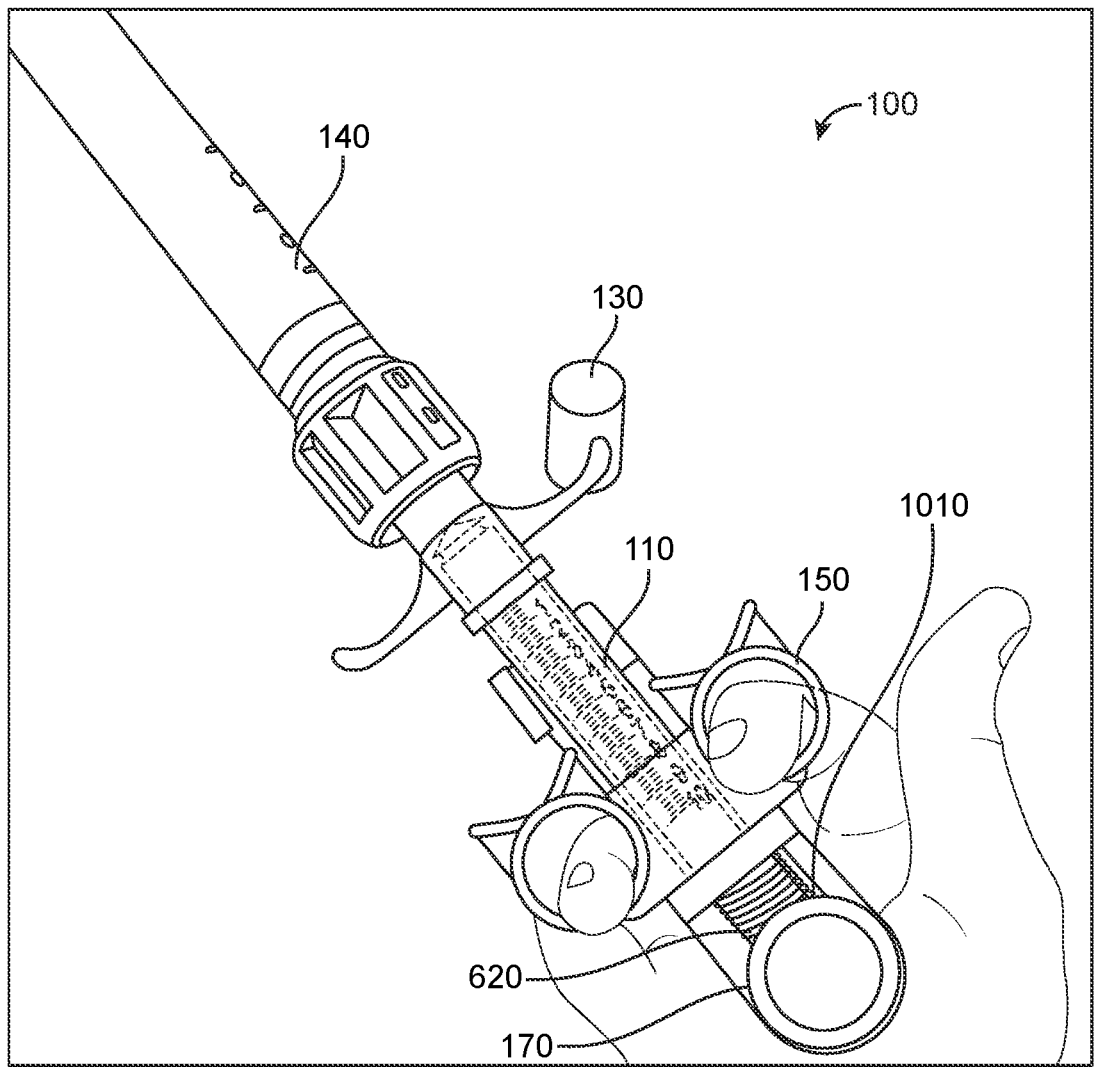
Figure 10B:
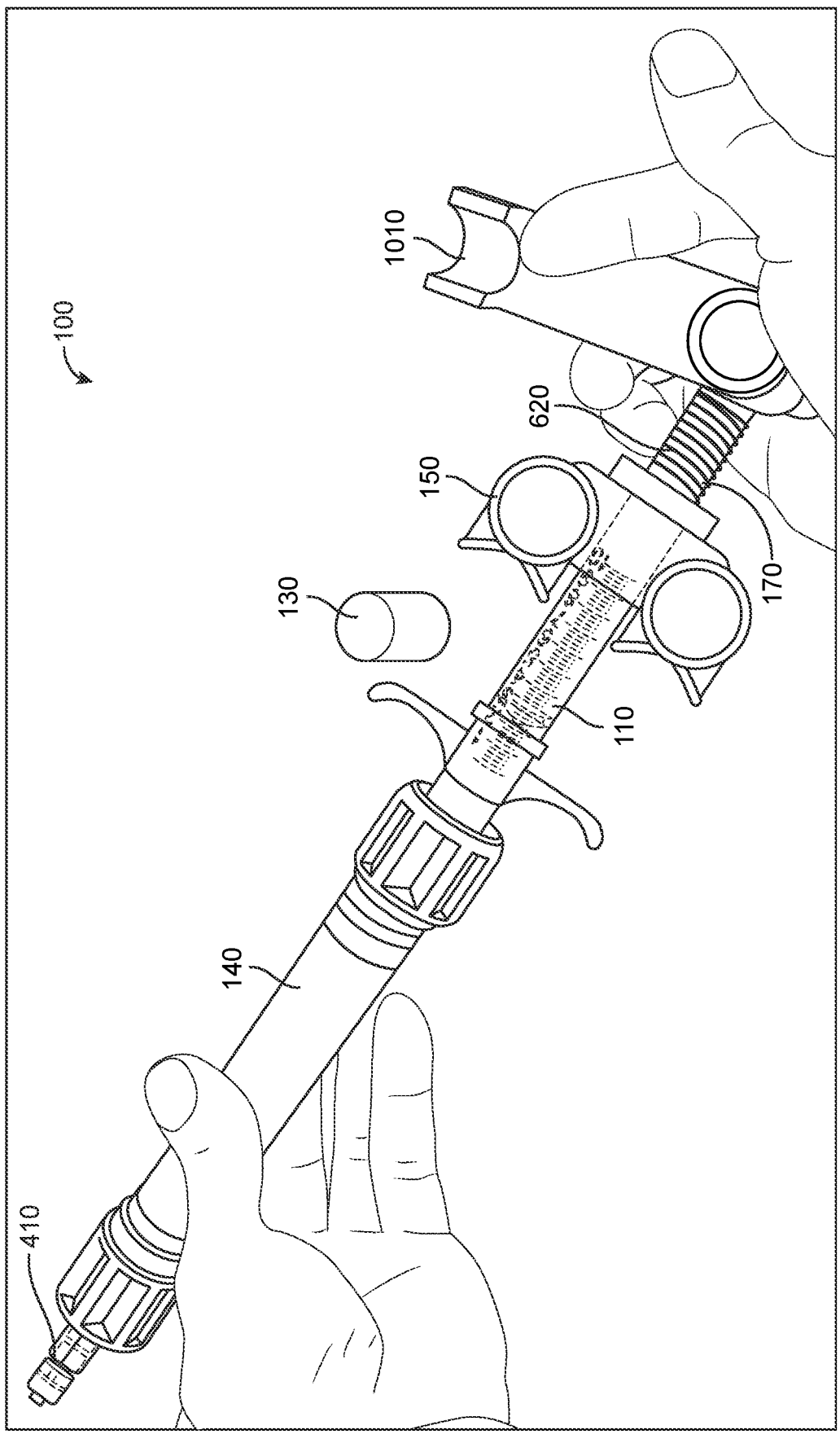
Figure 10C:
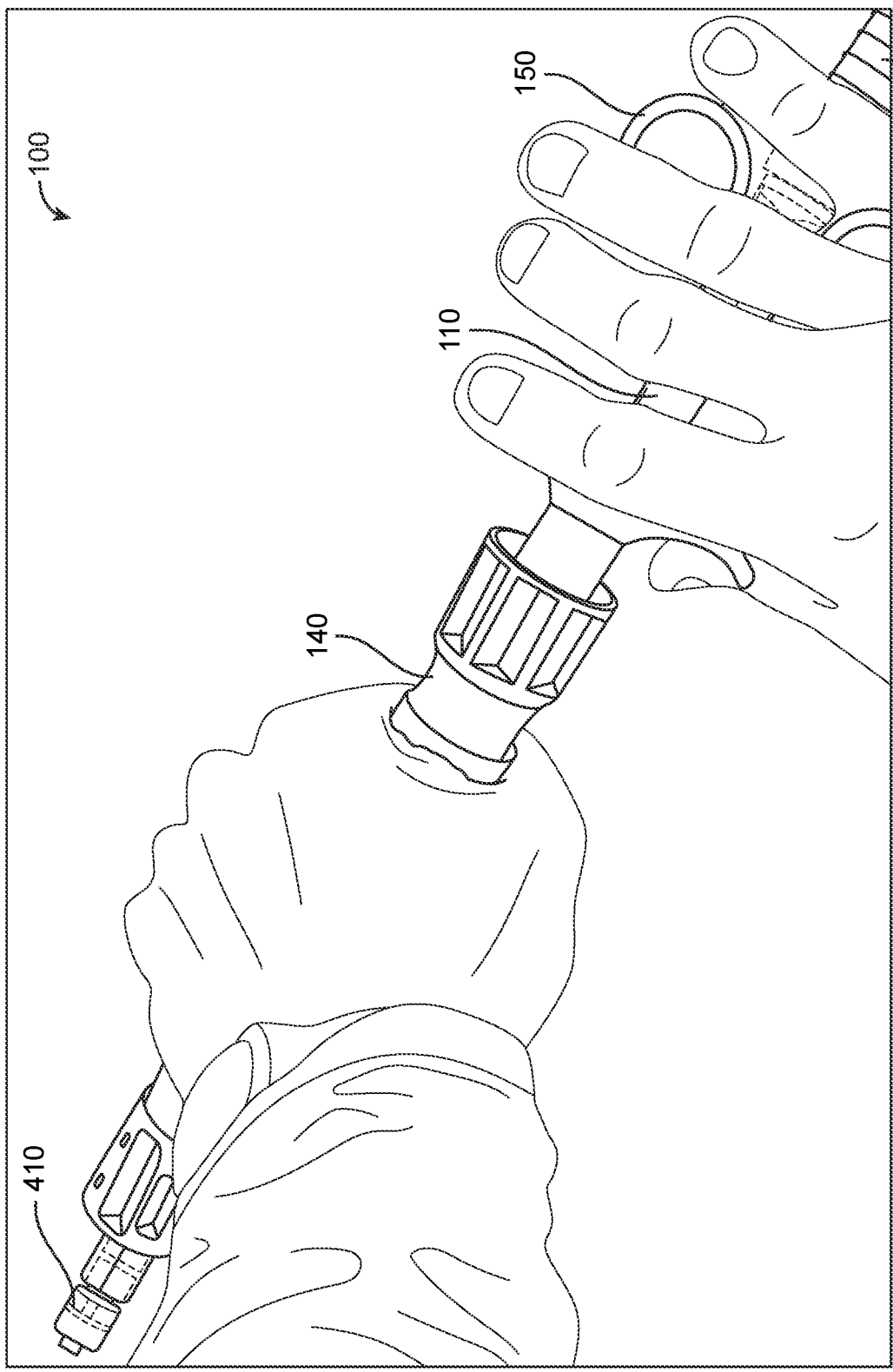
Figure 10D:
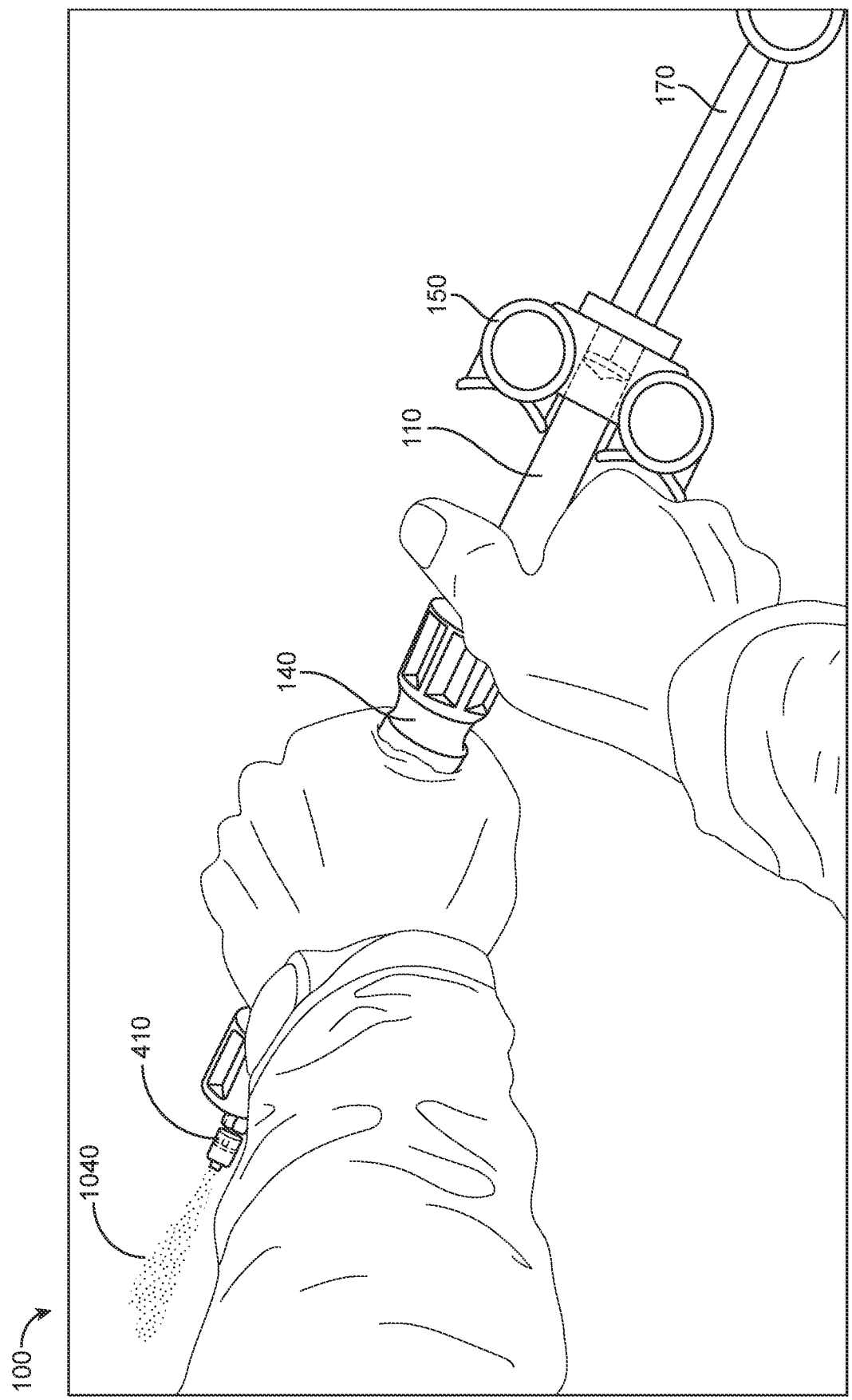
Figure 10E:
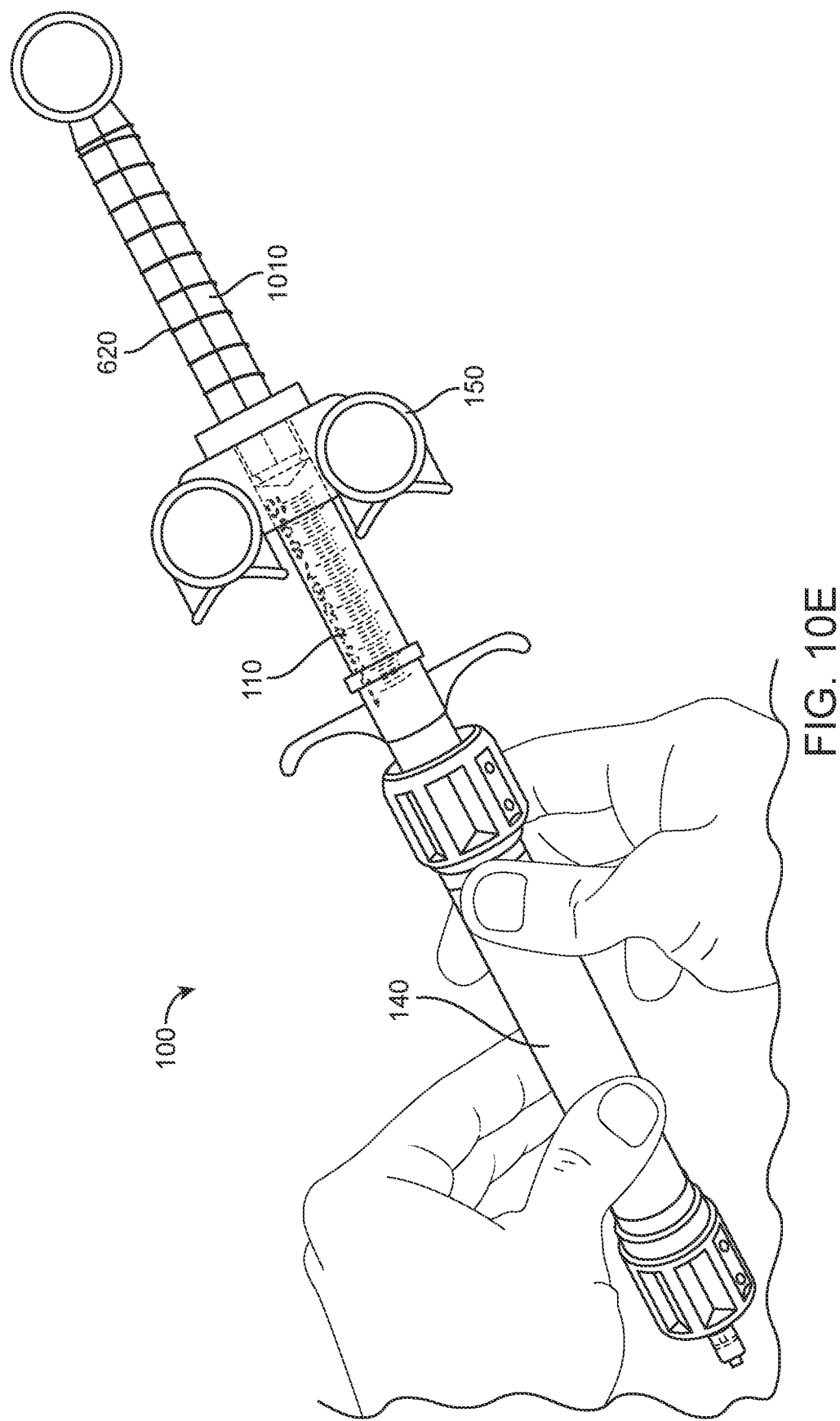
Figure 10F:
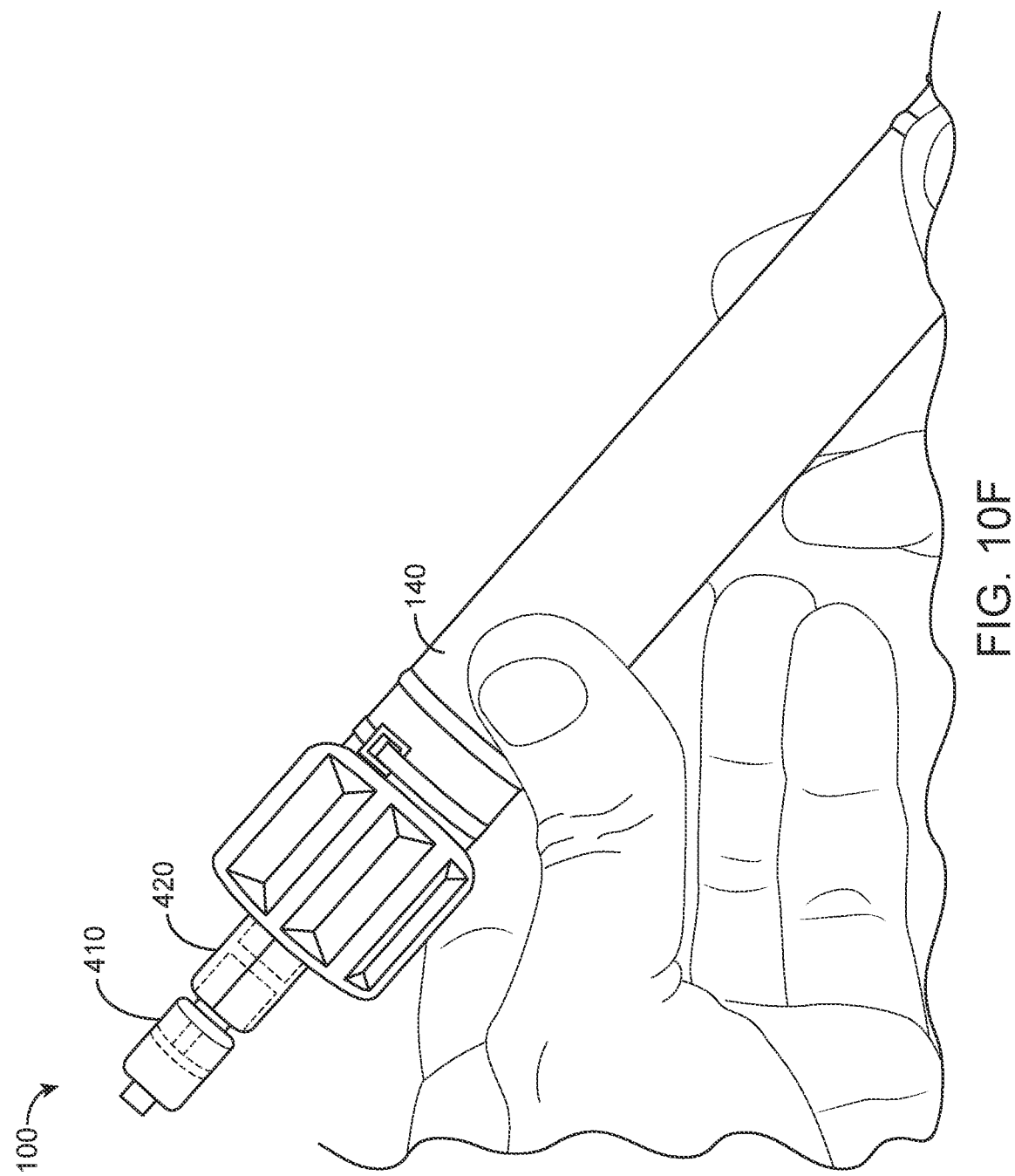
Figure 10H:
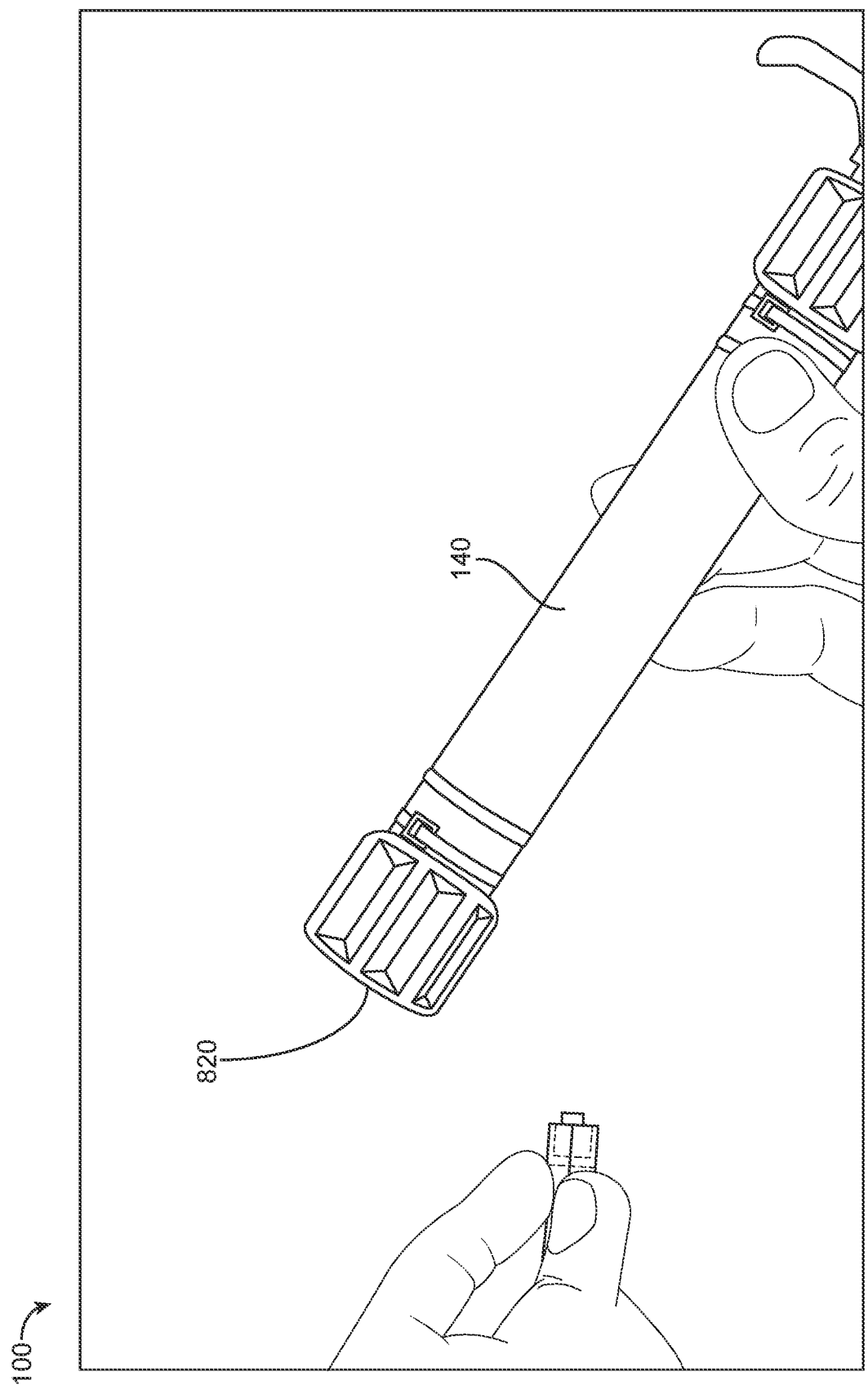
Figure 10I:
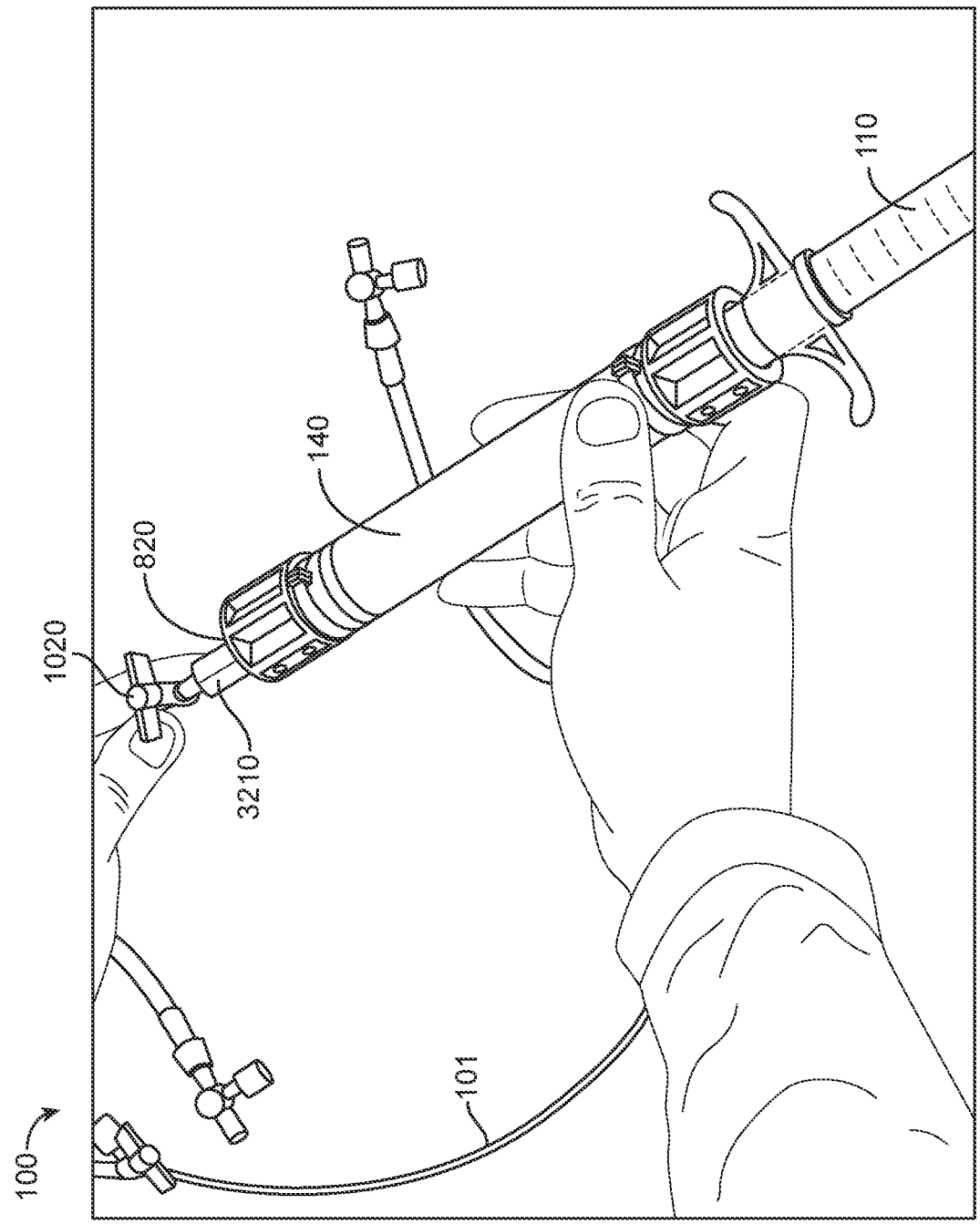
Figure 10J:
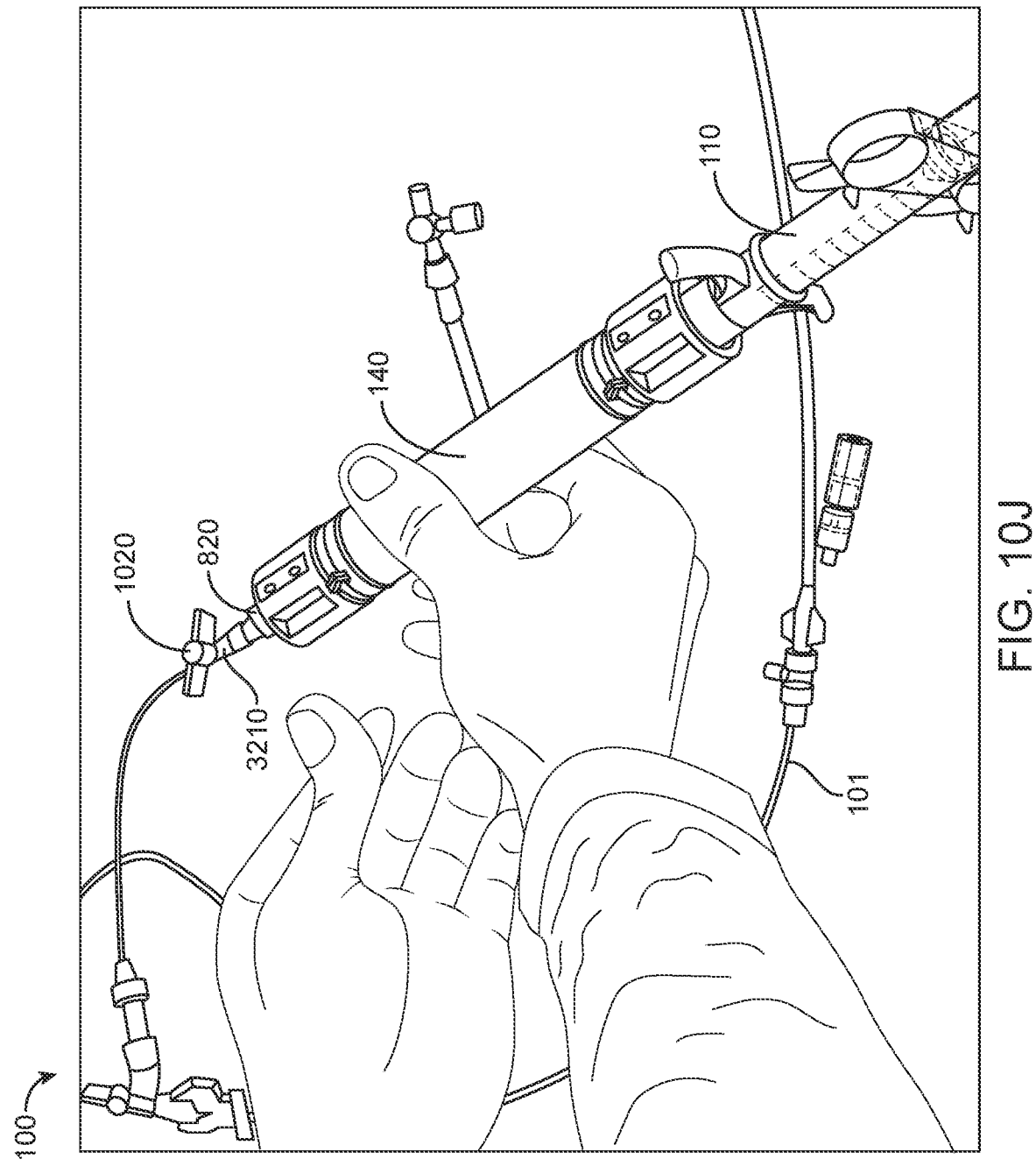
Figure 10K:
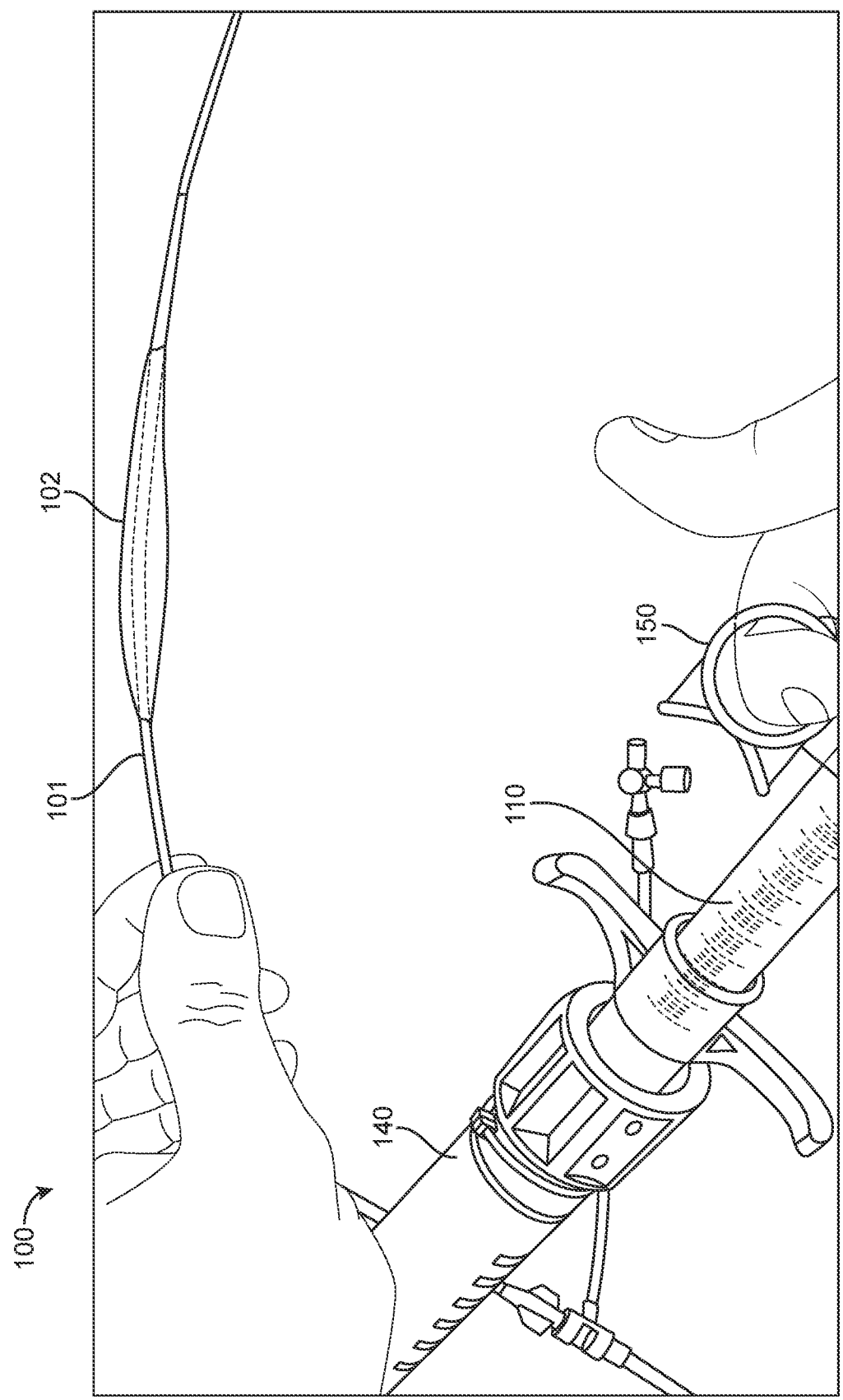
Figure 10L:
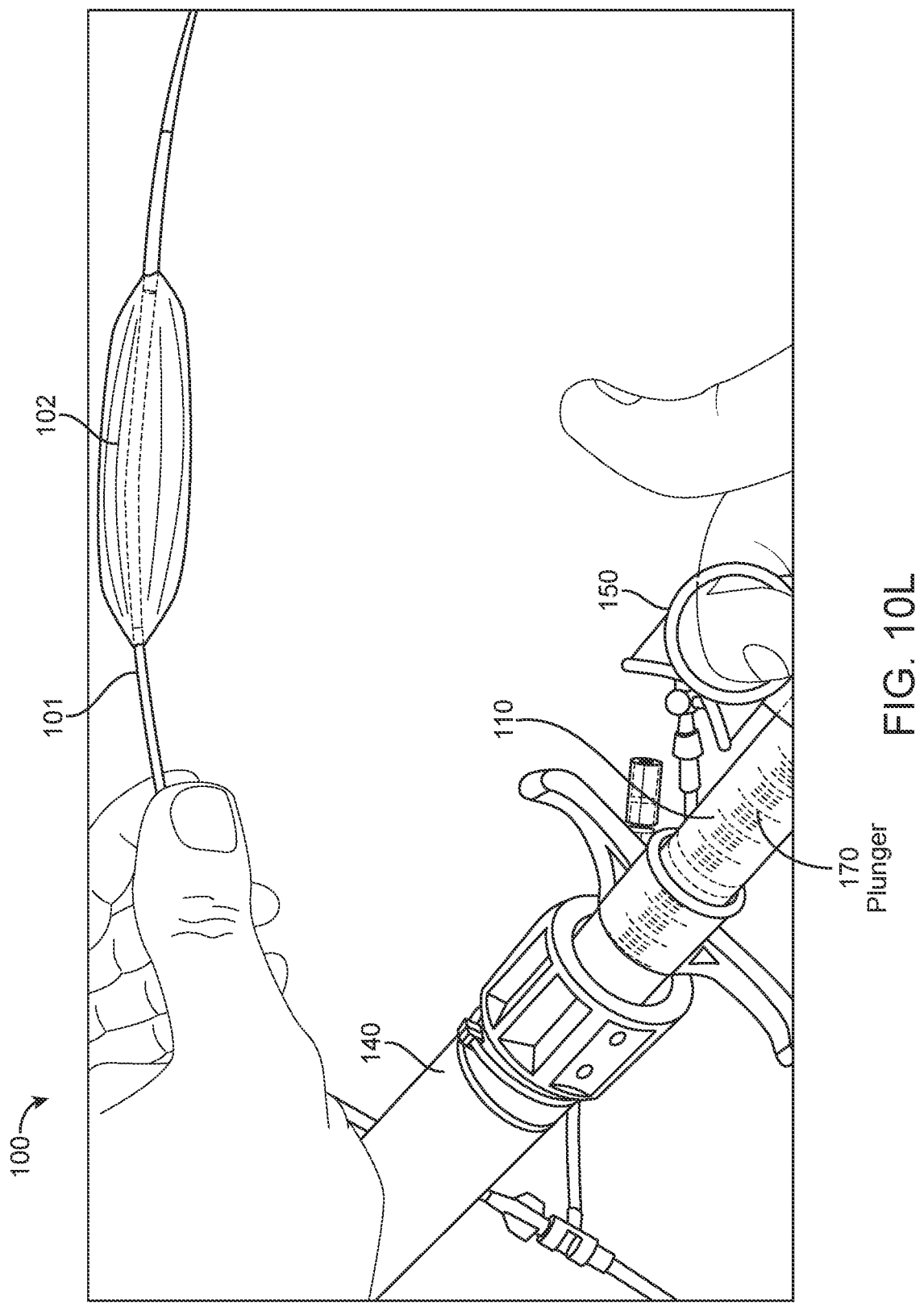

FIGS. 10A-10L show various steps involved in loading and using the inflation device of FIG. 9 to inflate a balloon of a balloon catheter. FIGS. 10A-10B show the first step of removing the plunger lock 1010. FIGS. 10C-10E show the second step of puncturing the compressed gas canister 470 and loading the syringe 110 with gas. FIGS. 10F-10H show the third step of removing of the one-way fitting 420 by the user. FIGS. 10I-10J show the fourth step of coupling a balloon catheter to the distal end of the device 100. FIGS. 10K-10L show the fifth step of inflating a balloon of the balloon catheter with the inflation device 100. Deflation of the balloon and decoupling of the catheter and the device 100 steps are not shown for succinctness.

FIG. 10A shows the inflation device 100 prior to use. The device 100 may comprise an optional plunger lock 1010 coupled to the plunger 170 and configured to prevent the plunger 170 from sliding within the syringe 110 prior to use by the user. Preventing the plunger 170 from moving may be useful for situations such as if the gas canister 470 is punctured during shipment or storage of the device 100 prior to use. In such cases, the gas would be released harmlessly from the device 100 without causing any other motion of the device 100 within its storage location.

FIG. 10B shows the plunger lock 1010 being rotated relative to the syringe 110 for removal.

FIG. 10C shows rotation of the handle 150 by the user. The plunger 170 may be in an unloaded position prior to rotation of the handle 150 and engagement of the puncture mechanism.

FIG. 10D shows the inflation device 100 at the moment just after engagement of the puncture mechanism. Rotation of the handle 150 may be configured to actuate (e.g., rotate) the syringe 110 from a first position to a second position relative to the puncture mechanism within the housing 140. Actuation of the syringe 110 from the first position to the second position may engage the puncture mechanism to put the syringe 110 into fluid communication with the compressed gas canister 470 such that the gas contained therein is loaded into the syringe 110 and the plunger 170 is moved from the unloaded position (FIG. 10C) and the loaded position (FIG. 10D). The pressure release mechanism may be fluidly coupled to the syringe 110 and configured to release excess gas 1040 after the puncture mechanism is engaged and the syringe 110 is loaded with a pre-determined volume of gas as described herein. The handle 150 may act like a stopper 160 to prevent the plunger 170 from moving past the loaded position when the gas is loaded into the syringe 110.

FIG. 10E shows the device after the syringe 110 has been loaded with the gas. The plunger 170 may be in a loaded position as described herein.

FIG. 10F shows the distal end of the device 100. The distal tip 820 may be coupled to a pressure relief mechanism 410 as described herein. The distal tip 820 may optionally have a one-way fitting 420 coupled thereto as a further safety mechanism as described herein. The one-way fitting 420 may prevent the distal tip 820 from being accidentally coupled to a catheter.

FIG. 10G shows removal of the pressure relief mechanism 410 and one-way fitting 420 from the distal tip 820.

FIG. 10H shows the pressure relief mechanism 410 and one-way fitting 420 removed and the distal tip 820 exposed and ready to be coupled to a balloon catheter for selectively inflating and deflating a balloon of the balloon catheter.

FIG. 10I shows coupling of coupling the distal tip 820 of the inflation device 100 to the catheter device 2800. The distal tip 820 may comprise a catheter fitting as described herein. The distal tip 820 may be configured to couple to a connection element 3210 of the catheter device 2800. The connection element 3210 may be coupled to a one-way valve 1020 to prevent flow of the gas from the distal tip 820 into the catheter when the valve 1020 is in the closed position as shown.

FIG. 10J shows the device 100 coupled to the catheter device 2800 with the valve 1020 coupled to the connection element 3210 in the open position, which may allow gas flow from the syringe 110 into the catheter 101 and to the balloon 102 of the balloon catheter 2800.

FIG. 10K shows the balloon 102 which may be fluidly coupled to the syringe 110 via the catheter 101 as described herein. The plunger 170 may be in the loaded position while the balloon 102 is in an uninflated configuration as shown.

FIG. 10L shows depression of the plunger 170 from the loaded position towards the unloaded position and injection of the gas from the syringe 110 into the catheter 101 via the outlet port to inflate the balloon 102.

Following inflation of the balloon, the balloon may be deflated as described herein. In some instances, deflation may comprise actuating the plunger 170 from the depressed position shown to the loaded position shown in FIG. 10K. In some instances, the device 100 may comprise a time-delay release mechanism, for example a spring 620, configured to deflate the balloon after a pre-determined amount of time following inflation of the balloon.

Although the steps above show a method of using an inflation device 100 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as desired to load the syringe 110, inflate the balloon, and/or perform the medical procedure of interest.

FIGS. 11A-11G show exemplary connection fittings for the distal tip 820 of the inflation device and a catheter, according to many embodiments. For example, the distal tip 820 may comprise a standard female swabable Luer connector 1110 as shown in FIGS. 11A-11F to act as a valve. The female swabable Luer connector 1110 may be configured to prevent gas flow from the inflation device 100 when nothing is coupled thereto. Connection of the female swabable Luer 1110 to a catheter 1120 may open the valve 1020 and fluidly couple the syringe 110 to the catheter 1120. The female swabable Luer may comprise a pusher element 1130 disposed within a deformable silicone coupler. The pusher may comprise a blunt cannula having one or more windows 1170 (shown in FIG. 11F). Connection of the female swabable Luer to the catheter may expose the one or more windows 1170 on the pusher 1130.

The catheter may comprise a connection element as described herein. The connection element may for example comprise a male swabable Luer connector 1140 as shown in FIGS. 11A-11C and 11G. The male swabable Luer 1140 may comprise a piston 1150 coupled to a pin spring 1160 disposed within a male Luer fitting housing 140. Connection of the distal tip 820 of the inflation device 100 may compress the spring 1160 and move the piston 1150 from a first position to a second position. Compression of the spring and movement of the piston may generate a vacuum within the balloon catheter device and remove any air or other gas from the catheter device prior to inflation and deflation with the gas loaded into the syringe 110 of the inflation device 100 as described herein.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments described herein may be employed in practicing the inventions of the present disclosure. It is intended that the following claims define the scope of the invention and that methods and structures within the scope of these claims and their equivalents be covered thereby.

What is claimed is:

1. A method for inflating a balloon catheter, the method comprising:
providing an inflation device, the inflation device comprising a housing, a compressed gas cartridge containing a gas disposed within the housing, a syringe disposed within the housing, and a puncture mechanism disposed within the housing, wherein the syringe has a first position and a second position relative to the puncture mechanism within the housing, and wherein actuation of the syringe from the first position to the second position engages the puncture mechanism to put the syringe into fluid communication with the compressed gas cartridge such that the gas contained is loaded into the syringe;
puncturing the compressed gas cartridge with the puncture mechanism in response to an actuation of the syringe from the first position to the second position, thereby loading the syringe with the gas;
preventing air from entering the syringe by maintaining the gas at a positive pressure relative to ambient pressure relative to ambient pressure after loading the syringe with the gas; and
coupling a distal tip of the inflation device to a catheter, the distal tip comprising an outlet port in fluid communication with the syringe, wherein the inflation device is configured to prevent the distal tip from coupling to the catheter prior to actuation of the syringe from the first position to the second position.

2. The method of claim 1, wherein the puncture mechanism comprises a pin, a needle, or a hollow tube.

3. The method of claim 1, wherein the gas comprises carbon dioxide.

4. The method of claim 1, wherein actuating the syringe from the first position to the second position comprises actuating a handle coupled to the housing from a first handle position to a second handle position.

5. The method of claim 1, further comprising positioning an expandable member of the catheter adjacent renal artery ostia of a patient.

6. The method of claim 5, further comprising injecting the gas from the syringe into the expandable member of the catheter in synchrony with an injection of a contrast media into the patient.

7. The method of claim 5, further comprising injecting the gas from the syringe into the expandable member of the catheter for preventing a contrast media from entering a renal artery of the patient.

8. The method of claim 1, further comprising injecting the gas from the syringe into the catheter via the outlet port and inflating an expandable member of the catheter.

9. The method of claim 8, wherein injecting the gas comprises depressing a plunger disposed within the syringe from a loaded position towards an unloaded position.

10. The method of claim 8, further comprising removing the compressed gas cartridge from the housing after injecting the gas.

11. The method of claim 8, further comprising deflating the balloon.

12. The method of claim 11, wherein deflating the balloon comprises actuating a plunger disposed within the syringe from an unloaded position to a loaded position.

13. The method of claim 11, wherein deflating the balloon occurs a pre-determined amount of time after injecting the gas and inflating the balloon.

14. The method of claim 1, wherein the inflation device comprises a one-way fitting coupled to the distal tip, wherein the one-way fitting is configured to be removed to expose the distal tip only when the syringe is in the second position.

15. The method of claim 14, further comprising removing the one-way fitting after actuating the syringe.

16. The method of claim 14, wherein the inflation device comprises a protection cap disposed around the one-way fitting and coupled to the housing, wherein the protection cap is configured to prevent removal of the one-way fitting when the syringe is in the first position and allow removal of the one-way fitting when the syringe is in the second position.

17. The method of claim 16, further comprising removing the protection cap after actuating the syringe.

18. The method of claim 1, further comprising adjusting a loading volume of the syringe to a pre-determined volume before actuating the syringe.

19. The method of claim 1, further comprising adjusting a volume of gas loaded into the syringe to a pre-determined volume after actuating the syringe.

20. The method of claim 1, wherein the compressed gas cartridge is configured to hold a first volume of gas that is greater than a second volume of gas which is loaded into the syringe and further comprising releasing excess gas after the puncture mechanism is engaged and the syringe is loaded with the second volume of gas.

21. The method of claim 1, wherein actuating the syringe from the first position to the second position comprises rotating the syringe from the first position to the second position.

* * * * *